(12) United States Patent
Hackl et al.

(10) Patent No.: US 11,339,440 B2
(45) Date of Patent: May 24, 2022

(54) MICRO-RNA SIGNATURES FOR THE PREDICTION OF LIVER DYSFUNCTION

(71) Applicants: TAmiRNA GmbH, Vienna (AT); Medizinische Universität Wien, Vienna (AT)

(72) Inventors: Matthias Hackl, Bisamberg (AT); Alice Assinger, Vienna (AT); Patrick Starlinger, Vienna (AT)

(73) Assignees: TAmiRNA GmbH, Vienna (AT); Medizinische Universität Wien, Vienna (AT)

( * ) Notice: Subject to any disclaimer, the term of this patent is extended or adjusted under 35 U.S.C. 154(b) by 0 days.

(21) Appl. No.: 17/278,624

(22) PCT Filed: Sep. 20, 2019

(86) PCT No.: PCT/EP2019/075319
§ 371 (c)(1),
(2) Date: May 26, 2021

(87) PCT Pub. No.: WO2020/058472
PCT Pub. Date: Mar. 26, 2020

(65) Prior Publication Data
US 2021/0269882 A1    Sep. 2, 2021

(30) Foreign Application Priority Data
Sep. 20, 2018    (AT) ............... A 50804/2018

(51) Int. Cl.
*C12Q 1/6883*    (2018.01)
*C12Q 1/6886*    (2018.01)

(52) U.S. Cl.
CPC ......... *C12Q 1/6883* (2013.01); *C12Q 1/6886* (2013.01); *C12Q 2600/118* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 5,912,148 A | 6/1999 | Eggerding |
| 6,130,073 A | 10/2000 | Eggerding |
| 6,258,568 B1 | 7/2001 | Nyren |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,115,400 B1 | 10/2006 | Adessi et al. |
| 7,169,560 B2 | 1/2007 | Lapidus et al. |
| 7,170,050 B2 | 1/2007 | Turner et al. |
| 7,282,337 B1 | 10/2007 | Harris |
| 7,302,146 B2 | 11/2007 | Turner et al. |
| 7,313,308 B2 | 12/2007 | Turner et al. |
| 7,329,492 B2 | 2/2008 | Hardin et al. |
| 7,476,503 B2 | 1/2009 | Turner et al. |
| 7,482,120 B2 | 1/2009 | Buzby |
| 7,501,245 B2 | 3/2009 | Quake et al. |
| 2013/0274147 A1 | 10/2013 | Eshoo et al. |
| 2014/0038831 A1 | 2/2014 | Suter et al. |
| 2014/0113978 A1 | 4/2014 | Barry et al. |
| 2016/0089453 A1 | 3/2016 | Zamore et al. |
| 2017/0166975 A1 | 6/2017 | Kondou et al. |

FOREIGN PATENT DOCUMENTS

| | | |
|---|---|---|
| CN | 101418343 A | 12/2008 |
| CN | 102776185 B | 5/2011 |
| EP | 2196543 A | 12/2008 |
| EP | 2829613 | 1/2015 |
| WO | 201114476 A1 | 2/2011 |
| WO | 2011076141 A1 | 6/2011 |
| WO | 2012151736 A1 | 11/2012 |
| WO | 2016036994 A1 | 3/2016 |
| WO | 2018231851 A1 | 12/2018 |

OTHER PUBLICATIONS

Sato et al PLoS One. 2011. 6(1): e16435, 10 pages and Table S3 (Year: 2011).*
International Preliminary Report on Patentability for corresponding International Patent Application No. PCT/EP2019/075319 dated Dec. 7, 2020.
Hao-Tu Zhu, et al., "Serum microRNA profiles as prognostic biomarkers for HBV positive hepatocellular carcinoma", ONCOTARGET, vol. 7, No. 29, p. 45637-45648 (2016).
Chiu-Ling Chen, et al., "Baculovirus-Mediated miRNA Regulation to Suppress Hepatocellular Carcinoma Tumorigenicity and Metastasis", Molecular Therapy, vol. 23, No. 1, pp. 79-88 (2015).
Jin-Lin Cheng, et al., "Plasma miRNA-122-5p and miRNA-151 a-3p identified as potential biomarkers for liver injury among CHB patients with PNAL T", Hepatology International. The 21st Conference of the Asian Pacific Association for the Study of the Liver, Springer India, India, vol. 12, No. 3, pp. 277-287 (2018).
Megan E. McNally, et al., "Concomitant dysregulation of microRNAs miR-151-3p and miR-126 correlates with improved survival in resected cholangiocarcinoma", HPB, vol. 15, No. 4, pp. 260-264 (2013).

(Continued)

*Primary Examiner* — Carla J Myers
(74) *Attorney, Agent, or Firm* — Loza & Loza, LLP; Michael F. Fedrick

(57) ABSTRACT

The invention relates to an in vitro method of determining a subjects risk of liver dysfunction, specifically after partial liver resection, said method comprising the steps of providing a sample from said subject, determining in said sample the expression level of at least one miRNA, selected from the group consisting of miR-151a, miR-192 and miR-122, and comparing these expression level(s) with at least one reference expression level, or identifying the ratios of the expression levels of miR-15 1a to miR-192 and/or of miR-122 to miR-151a and comparing said expression level ratios with reference expression level ratios, and classifying the sample from the outcome of the comparison into one of at least two classes, wherein each class is one of the at least two categories "high-risk" and "low-risk".

13 Claims, 13 Drawing Sheets

Figure 1:
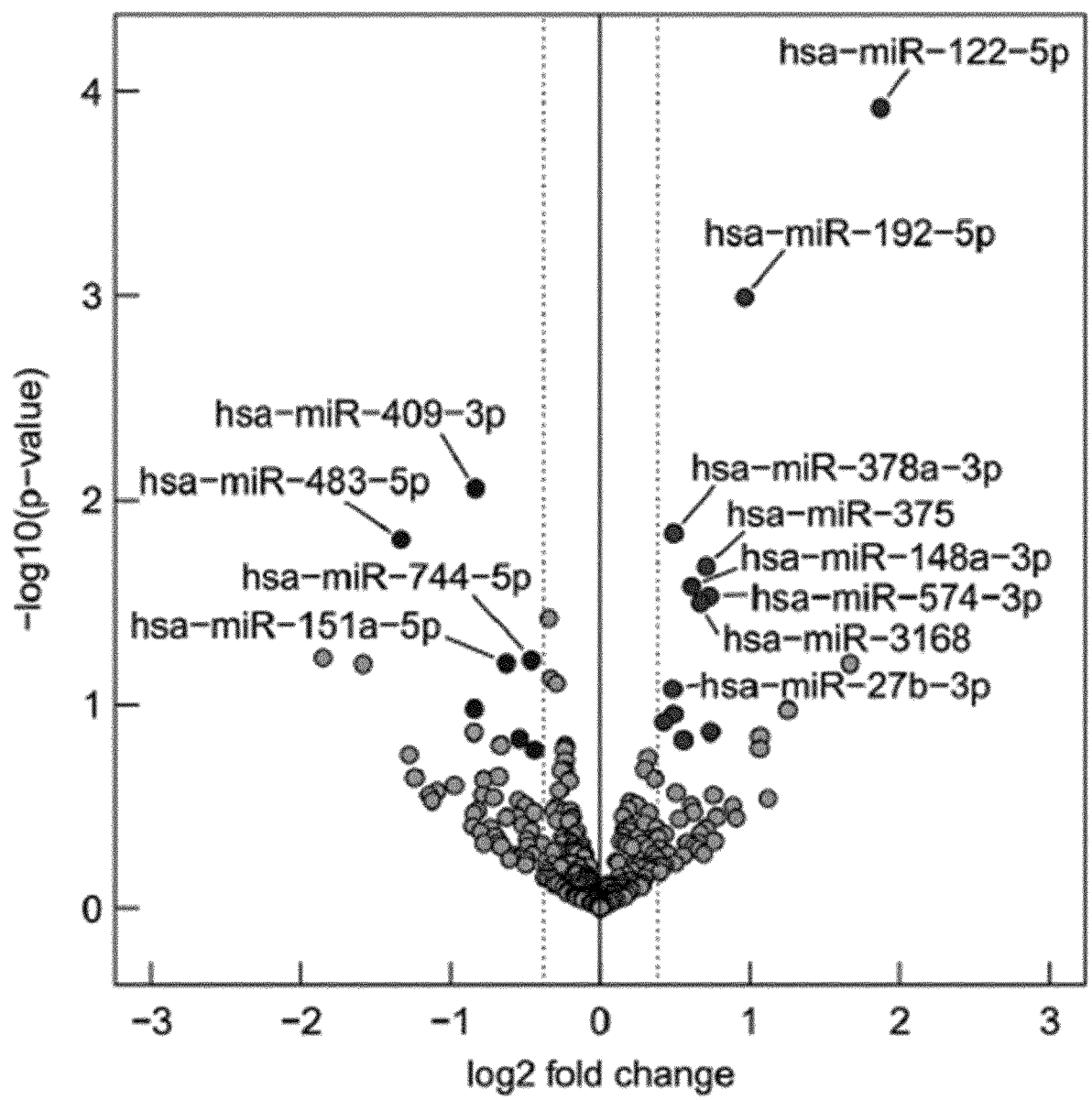

Specification includes a Sequence Listing.

(56) References Cited

OTHER PUBLICATIONS

Goh Eun Chung, et al., "High expression of microRNA-15b predicts a low risk of tumor recurrence following curative resection of hepatocellular carcinoma", Oncology Reports, vol. 23, No. 1, pp. 113-119 (2010).
Fumiaki Sato, et al., "MicroRNA Profile Predicts Recurrence after Resection in Patients with Hepatocellular Carcinoma within the Milan Criteria", Plos One, vol. 6, No. 1, p. e16435 (2011).
Arya et al., "Basic principles of real-time quantitative PCR" Expert review of molecular diagnostics. vol. 5, No. 2, pp. 209-219 (2005). DOI: 10.1586/14737159.5.2.209.
Bartel, "MicroRNAs: Genomics, Biogenesis, Mechanism, and Function," Cell. vol. 116, Issue 2, pp. 281-297 (2004). DOI: 10.1016/S0092-8674(04)00045-5.
Behjati et al., "What is next generation sequencing?", Arch Dis Child Educ Pract Ed., vol. 98, No. 6: pp. 236-238 (2013) DOI: 10.1136/archdischild-2013-304340.
Blondal et al., "Assessing sample and miRNA profile quality in serum and plasma or other biofluids," Methods. vol. 59, No. 1, pp. S1-S6, (2013). DOI: 10.1016/j.ymeth.2012.09.015.
Boleslawski et al., "Hepatic venous pressure gradient in the assessment of portal hypertension before liver resection in patients with cirrhosis," British Journal of Surgery, vol. 99, No. 6, pp. 855-863 (2012). DOI: 10.1002/bjs.8753.
Dindo et al., "Classification of Surgical Complications: A New Proposal With Evaluation in a Cohort of 6336 Patients and Results of a Survey," Annals of Surgery, vol. 240, No. 2, pp. 205-213 (2004). DOI: 10.1097/01.sla.0000133083.54934.ae.
Forbes et al., "Liver regeneration—mechanisms and models to clinical application," Nat Rev Gastroenterol Hepatol., vol. 13, No. 8, pp. 473-485 (2016). DOI: 10.1038/nrgastro.2016.97.
Friedman et al., "Most mammalian mRNAs are conserved targets of microRNAs," Genome Research. vol. 19, No. 1, pp. 92-105 (2009). DOI: 10.1101/gr.082701.108.
Hackl et al., "Circulating microRNAs as novel biomarkers for bone diseases—Complex signatures for multifactorial diseases?" Molecular and Cellular Endocrinology, vol. 432, pp. 83-95 (2016). DOI: 10.1016/j.mce.2015.10 015.
Haegele et al., "Perioperative Non-Invasive Indocyanine Green-Clearance Testing to Predict Postoperative Outcome after Liver Resection," PLoS One, vol. 11, No. 11, p. e0165481 (2016). DOI: 10.1371/journal.pone.0165481.
Head et al., "Library construction for next-generation sequencing: Overviews and challenges," Biotechniques. vol. 56, No. 2, pp. 61-77 (2014) (Author manuscript). DOI: 10.2144/000114133.
Hidaka et al., "Intraoperative portal venous pressure and long-term outcome after curative resection for hepatocellular carcinoma," British Journal of Surgery. vol. 99, No. 9, pp. 1284-1289 (2012). DOI: 10.1002/bjs.8861.
Bari et al., "Treatment of portal hypertension," World J Gastroenterol. vol. 18, No. 11, pp. 1166-1175 (2012). DOI: 10.3748/wjg.v18.i11.1166.
Kocijan et al., Circulating microRNA Signatures in Patients With Idiopathic and Postmenopausal Osteoporosis and Fragility Fractures, J Clin Endocrinol Metab. vol. 101, No. 11, pp. 4125-4134 (2016). DOI: 10.1210/jc.2016-2365.
Krieger et al., "Evaluation of Chemotherapy-Associated Liver Injury in Patients with Colorectal Cancer Liver Metastases Using Indocyanine Green Clearance Testing," Ann Surg Oncol. vol. 18, No. 6, pp. 1644-1650 (2011). DOI: 10.1245/S10434-010-1494-1.
La Mura et al., "Cirrhosis and portal hypertension: The importance of risk stratification, the role of hepatic venous pressure gradient measurement," World J Hepatol. vol. 8, No. 7, pp. 688-695 (2015). DOI: 10.4254/wjh.v7.i4.688.
Lafaro et al., "Defining Post Hepatectomy Liver Insufficiency: Where do We stand?" J Gastrointest Surg. vol. 19, No. 11, pp. 2079-2092 (2015). DOI: 10.1007/s11605-015-2872-6.
Lecellier et al., "A Cellular MicroRNA Mediates Antiviral Defense in Human Cells," Science. vol. 308, No. 5721, pp. 557-560 (2005). DOI: 10.1126/science.1108784.
Luo, "MicroRNA Expression Analysis Using the Illumina MicroRNA-Seq Platform," Methods Mol Biol. vol. 822, pp. 183-188 (2012). DOI: 10.1007/978-1-61779-427-8_12.
Metzker, "Sequencing technologies—the next generation," Nat Rev Genet. vol. 11, No. 1, pp. 31-46 (2010). DOI: 10.1038/nrg2626.
Mitchell et al., "Circulating microRNAs as stable blood-based markers for cancer detection," Proc Natl Acad Sci USA. vol. 105, No. 30, p. 105113-10518 (2008). DOI: 10.1073/pnas.0804549105.
Montani et al., "miR-Test: A Blood Test for Lung Cancer Early Detection," J Natl Cancer Inst. vol. 107, No. 6, p. djv063 (2015). DOI: 10.1093/jnci/djv063.
Mussbacher et al., "Optimized plasma preparation is essential to monitor platelet-stored molecules in humans," PLoS One. vol. 12, No. 12, p. e0188921 (2017). DOI: 10.1371/journal pone.0188921.
Navarro et al., "Real-time PCR detection chemistry," Clin Chim Acta. vol. 439, pp. 231-250 (2015). DOI: 10.1016/j.cca.2014.10.017.
Qadan et al., "Management of Postoperative Hepatic Failure," J Am Coll Surg. vol. 222, No. 2, pp. 195-208 (2016). DOI: 10.1016/j.jamcollsurg.2015.11.007.
Rahbari et al., "Posthepatectomy liver failure: A definition and grading by the International Study Group of Liver Surgery (ISGLS)," Surgery. vol. 149, No. 5, pp. 713-724 (2011) DOI: 10.1016/j.surg.2010.10.001.
Schiergens et al., "Thirty-day mortality leads to underestimation of postoperative death after liver resection: A novel method to define the acute postoperative period," Surgery. vol. 48, No. 6, pp. 1530-1537 (2015). DOI: 10.1016/j.surg.2015.07.019.
Schmittgen et al., "Real-time PCR quantification of precursor and mature microRNA," Methods. vol. 44, No. 1, pp. 31-38 (2008). DOI: 10.1016/j.ymeth.2007.09.006.
Schnitzbauer et al., "Right Portal Vein Ligation Combined With In Situ Splitting Induces Rapid Left Lateral Liver Lobe Hypertrophy Enabling 2-Staged Extended Right Hepatic Resection in Small-for-Size Settings," Ann Surg. vol. 255, No. 3, pp. 405-414 (2012). DOI: 10.1097/SLA.0b013e31824856f5.
Sozzi et al., "Clinical Utility of a Plasma-Based miRNA Signature Classifier Within Computed Tomography Lung Cancer Screening: A Correlative MILD Trial Study," J Clin Oncol. vol 32, No. 8, pp. 768-773 (2014). DOI: 10.1200/JCO.2013.50.4357.
Starlinger et al., "Platelet-stored angiogenesis factors: Clinical monitoring is prone to artifacts," Dis Markers. vol. 31, No. 2, pp. 55-65 (2011). DOI: 10.3233/DMA-2011-0798.
Starlinger et al., "Predicting Postoperative Liver Dysfunction Based on Blood-Derived MicroRNA Signatures," Hepatology. vol. 69, No. 6, pp. 2636-2651 (2019). DOI: 10.1002/hep.30572.
Strasberg et al., "Use and Dissemination of the Brisbane 2000 Nomenclature of Liver Anatomy and Resections," Ann Surg. vol. 257, No. 3, pp. 377-382 (2013) DOI: 10.1097/SLA.0b013e31825a01f6.
Stremitzer et al., "Value of hepatic venous pressure gradient measurement before liver resection for hepatocellular carcinoma," British Journal of Surgery. vol. 98, No. 12, pp. 1752-1758 (2011). DOI: 10.1002/bjs.7672.
Van Rooij et al., "A signature pattern of stress-responsive microRNAs that can evoke cardiac hypertrophy and heart failure," Proc Natl Acad Sci USA. vol. 103, No. 48, p. 18255-18260 (2006). DOI: 10.1073/pnas.0608791103.
Wang et al., "MicroRNA as Biomarkers and Diagnostics," J Cell Physiol. vol. 231, No. 1, pp. 25-30 (2016). DOI: 10.1002/jcp.25056.
International Patent Application No. PCT/EP2019/075319. Written Opinion of the International Preliminary Examining Authority dated Jul. 21, 2020.
International Patent Application No. PCT/EP2019/075319. International Search Report dated Nov. 18, 2019.
Corresponding Austrian Patent Application No. 50804/2018, Provisional Decision mailed Apr. 4, 2019.
McNally M E et al., HPB Oxford, 2013, vol. 15, No. 4, pp. 260-264.
Zhu H T et al., Oncotarget, 2016, vol. 7, No. 29, p. 45637-45648.

(56) References Cited

OTHER PUBLICATIONS

Office Action in corresponding Japanese Patent Application No. 2021-529262 dated Sep. 6, 2021.

\* cited by examiner

Fig. 3D
Fig. 3E
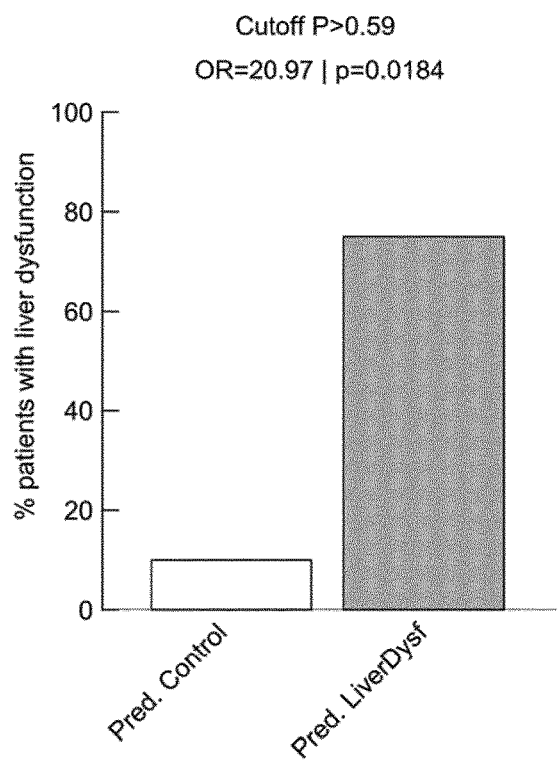
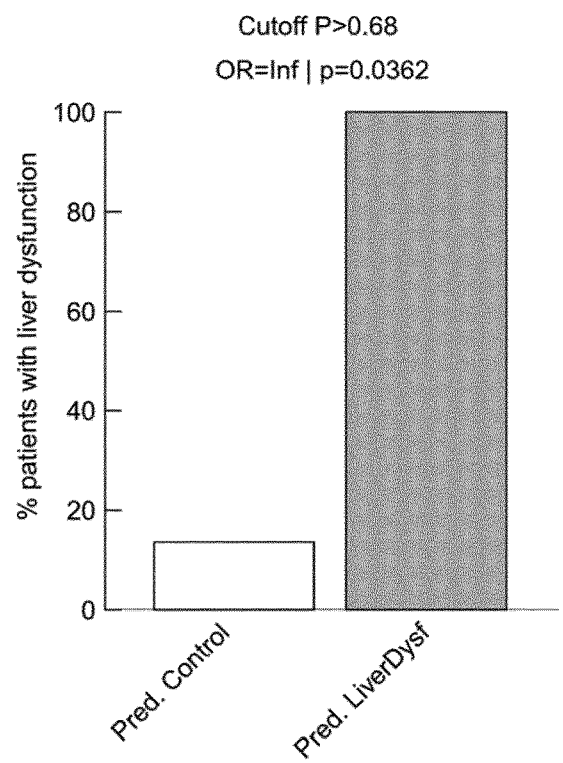

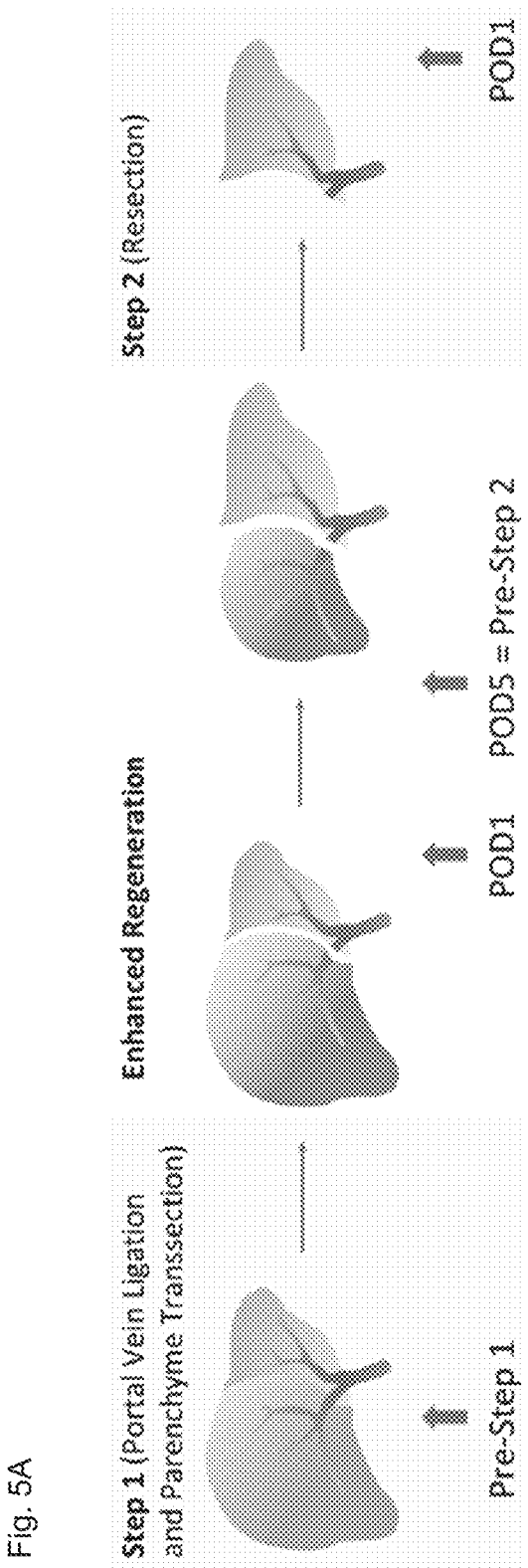

MICRO-RNA SIGNATURES FOR THE PREDICTION OF LIVER DYSFUNCTION

CROSS-REFERENCE TO RELATED APPLICATIONS

This application is the U.S. national stage of International Patent Application No. PCT/EP2019/075319, filed on Sep. 20, 2019, which claims the benefit of priority under 35 U.S.C. § 119(e) from Austrian Patent Application No. A 50804/2018, filed Sep. 20, 2018. The disclosures of the foregoing applications are incorporated herein by reference in their entirety.

SEQUENCE LISTING

The entire content of a Sequence Listing titled "Sequence_Listing.txt," created on Mar. 22, 2021 and having a size of 2 kilobytes, which has been submitted in electronic form in connection with the present application, is hereby incorporated by reference herein in its entirety.

FIELD OF THE INVENTION

The present invention provides a method, specifically an in vitro method, to determine a subject's risk of liver dysfunction, in particular following liver resection, wherein the level of one or more selected miRNAs is quantified in a sample from said subject.

BACKGROUND OF THE INVENTION

Liver resection represents the only curative treatment in many liver malignancies. Post-resectional hepatic regeneration is the main determinant for clinical outcome of patients undergoing liver resection (1), as insufficient hepatic regeneration after liver resection was shown to result in postoperative liver dysfunction (LD), which occurs in up to 30% of patients after major hepatic resections (2). Importantly, currently available treatment options for patients with postoperative LD are very limited, mostly symptomatic and goal-directed (2, 3). Hence, risk stratification for optimized patient selection prior to liver surgery is key for minimizing the incidence of postoperative LD and concomitant complications. Furthermore, identifying patients at risk of developing liver dysfunction, not only following liver resection, as well as monitoring patient response to treatments aiming to stimulate liver regeneration is essential to provide optimal patient care. However, currently available markers are often expensive, time consuming and sometimes invasive, highlighting the need for an easily assessable test to determine liver dysfunction and to predict postoperative liver function recovery.

Emerging evidence suggests that microRNA (miRNA) signatures represent potent diagnostic, prognostic and treatment response biomarkers for several diseases (4). As master regulators of expression of multiple genes in different tissues, miRNAs can control virtually every cellular process on a transcriptional level, including cellular development, proliferation, migration, survival, metabolism, homeostasis and regeneration (5). Estimates based on computational analyses suggest that over 50% of the human transcriptome is regulated by at least one miRNA (6). Hence, it is not surprising that aberrant miRNA expression can have detrimental effects on signaling pathways and indeed has been implicated with a wide range of diseases (7-9). To date, almost 2000 miRNAs have been identified and some have already been validated for in vitro diagnosis and/or prognosis of various malignant diseases, demonstrating their potential as biomarkers in the clinic (10-12).

For example, WO2011/076141A1 and EP2196543A1 provide microRNA biomarkers for the diagnosis of hepatocellular cancer. WO2012/151736A1 discloses microRNA biomarkers which can be used to diagnose hepatocellular carcinoma or to distinguish between hepatocellular carcinoma and chronic hepatitis B or cirrhosis. WO2016/036994A1, for example, uses microRNA profiling in combination with further biomarkers, such as oncogenes, for the diagnosis of liver cancer.

US20170166975A1 discloses a kit or device for the detection of liver cancer, comprising a nucleic acid capable of specifically binding to microRNA in a patient sample.

CN101418343A discloses a kit for predicting postoperative liver cancer relapse of early primary liver cancer patients.

Micro RNAs have also been discovered as biomarkers for diseases other than malignancies. WO2018/231851A1, for example, discloses a method of diagnosing nonalcoholic steatohepatitis (NASH) or liver fibrosis, wherein the levels of one or more microRNAs are detected in a patient sample.

Besides highly tissue-specific expression profiles of some miRNAs, they also offer several other beneficial features sought after in biomarkers—e.g. miRNAs are easily accessible from biofluids such as blood, urine and saliva via non-invasive methods. Furthermore, they exhibit high stability and relatively low complexity (e.g. no post-processing modifications) and can be readily assessed by various methods with high specificity that also allow for signal amplification, making them superior compared to other classes of biomarkers including DNA, RNA and proteins.

Micro RNAs have also been used to modulate the translation of target mRNA. US2016089453A1, for example, discloses RNA modulating agents using miR-122 as guide to modify mRNA in hepatocytes.

Despite such advancements, treatment options as well as reliable predictive markers to determine patients at risk to develop LD, in particular after surgery, are limited. Accordingly, there is an urgent need for an easily assessable test to predict the risk of developing liver dysfunction and to monitor treatment response to liver regeneration stimulation, specifically as current markers are often expensive, time consuming and sometimes invasive.

SUMMARY

It is the objective of the present invention, to provide reliable biomarkers, with high specificity and validity, for the prediction of liver dysfunction, in particular after partial liver resection and for the monitoring of liver function, in particular following partial liver resection or liver regeneration stimulation.

The problem is solved by the present invention.

The inventors have shown that expression levels of specific miRNAs are significantly altered in patients who developed liver dysfunction after partial liver resection compared to patients who did not develop liver dysfunction. Surprisingly, these changes in expression levels were shown in blood samples derived from patients before surgery and thus enable reliable prediction of development of liver dysfunction. Further, the risk of developing liver dysfunction after partial liver resection can be predicted with precision even before surgery.

The present invention provides a selected set of miRNAs that are specifically up- or down-regulated and are thus useful as valuable biomarkers and represent a diagnostic and predictive signature applicable over a broad range of liver diseases.

According to the invention there is provided an in vitro method of determining a subject's risk of liver dysfunction, specifically after partial liver resection, said method comprising the steps of:

a) providing a sample from said subject, b) determining in said sample the expression level of at least one miRNA, selected from the group consisting of miR-151a, miR-192 and miR-122, and i. comparing the expression level(s) of b) with at least one reference expression level, or ii. identifying the ratios of miR-151a to miR-192 and/or of miR-122 to miR-151a based on the expression levels determined in b), and comparing said expression level ratios with reference expression level ratios, and classifying the sample from the outcome of the comparison of step i) or step ii) into one of at least two classes, wherein each class is one of the at least two categories "high-risk" and "low-risk".

Specifically, the in vitro method provided herein allows determining a subject's risk of developing liver dysfunction. Preferably, the in vitro method provided herein allows determining a subject's risk of developing liver dysfunction after partial liver resection.

Specifically, in a patient's sample the expression level of at least one miRNA selected from the group consisting of miR-151a, miR-192 and miR-122 is determined. Specifically, the expression level of at least two of miR-151a, miR-192 and miR-122 is determined. Specifically, the expression level of miR-151a and miR-192 is determined. Specifically, the expression level of miR-151a and miR-122 is determined. Specifically, the expression level of miR-192 and miR-122 is determined.

According to a specific embodiment, the expression levels of miR-151a, miR-192 and miR-122 are determined.

Specifically, the miRNAs used herein are selected from the group consisting of hsa-miR-151a-5p, hsa-miR-192-5p and hsa-miR-122-5p.

Specifically, a decreased expression level of miR-151a is indicative of increased risk of liver dysfunction. Specifically, an increased expression level of miR-122 and/or miR-192 is indicative of increased risk of liver dysfunction.

Specifically, in pre-surgical samples of patients with increased risk of liver dysfunction the expression level of miR-151a is down-regulated. Specifically, in pre-surgical samples of patients with increased risk of liver dysfunction the expression level of miR-122 and/or the expression level of miR-192 is up-regulated. Specifically, pre-surgical samples are samples provided from a patient before partial liver resection.

According to a specific embodiment, the outcome of the comparison of step i) or step ii) can be classified into further classes of the categories "no-risk" and "medium-risk". Specifically, comparing the miRNA expression levels or expression level ratios in a subject's sample to the miRNA expression levels or expression level ratios in samples of subjects which did not develop liver dysfunction after partial liver resection or to samples of healthy subjects allows classification of a subject's sample into one of the categories "no-risk", "low-risk", "medium-risk" or "high-risk".

Specifically, a subject, whose sample is classified as belonging to the category "no risk", thus, has no risk or very low risk of developing liver dysfunction, in particular after partial liver resection. Preferably, no risk or very low risk refers to a risk of 25% or less than 25% to develop liver dysfunction. A subject, whose sample is classified as belonging to the category "low risk", thus, has a low risk of developing liver dysfunction after partial liver resection. Preferably, low risk refers to a risk of more than 25% and up to 50% to develop liver dysfunction. A subject, whose sample is classified as belonging to the category "medium risk", thus, has a medium risk of developing liver dysfunction after partial liver resection. Preferably, medium risk refers to a risk of more than 50% and up to 75% to develop liver dysfunction. A subject, whose sample is classified as belonging to the category "high risk", thus, has a high risk of developing liver dysfunction after partial liver resection. Preferably, high risk refers to a risk of more than 75% to develop liver dysfunction.

Specifically, the reference expression level is the expression level of at least one miRNA, selected from the group consisting of miR-151a, miR-192, and miR-122 of a healthy subject or a subject without post-operative liver dysfunction or a group or pool thereof.

Specifically, reference expression level ratios are expression level ratios of miR-151a to miR-192 and of miR-122 to miR-151a of a healthy subject or a subject without post-operative liver dysfunction or a group thereof.

Specifically, said reference expression level can be the average level of corresponding miRNAs in subjects which did not develop liver dysfunction after partial liver resection, specifically in a pool of samples derived from such subjects, wherein a difference by more than one standard deviation, specifically by about 1.1, 1.2, 1.3, 1.4, 1.5, 1.6, 1.7, 1.8, 1.9, specifically about 2 standard deviations or more is indicative of increased risk of developing liver dysfunction after partial liver resection. Specifically, a difference in the miRNA expression level or in the miRNA expression level ratios compared to the expression levels or expression level ratios of corresponding miRNAs in subjects who did not develop liver dysfunction after partial liver resection by at least 1.3 fold is indicative of increased risk of developing liver dysfunction.

Specifically, a difference by more than 1.5 standard deviations, preferably more than 2 standard deviations, specifically about 2.1, 2.2, 2.3, 2.4, 2.5 or 3 is indicative of high risk of developing liver dysfunction, specifically after partial liver resection.

Specifically, a difference by at least one standard deviation is indicative of medium risk of developing liver dysfunction, specifically after partial liver resection.

Specifically, a difference by less than one standard deviation is indicative of low risk of developing liver dysfunction, specifically after partial liver resection.

Specifically, miRNA expression levels or expression level ratios which are comparable to the corresponding reference expression levels or reference expression level ratios, specifically which levels or ratios differ by no more than 0.5 standard deviations from reference levels or reference ratios are indicative of very low risk of developing liver dysfunction, specifically after partial liver resection. Such samples can thus be classified as belonging to the category "no-risk". A subject whose sample is classified as belonging to the category of "no-risk" is less likely to develop liver dysfunction after partial liver resection than a subject whose sample is classified as belonging to the category "low-risk".

It is within the embodiment of the invention to use either a single reference sample from a healthy subject or a subject which did not develop liver dysfunction after partial liver resection or a pool of samples derived from healthy subjects or subjects which did not develop liver dysfunction after partial liver resection for comparison with the respective sample from the subject whose LD risk to be determined. Said pool can consist of 2, 3, 4, 5, 6, 7, or more samples, specifically up to 10, 100 or more than 100 samples from different individuals.

According to a specific embodiment of the invention, subjects classified as "low-risk" are subjected to partial liver resection, subjects classified as "medium-risk" are subjected to stimulation of liver regeneration before partial liver resection and subjects classified as "high-risk" are not subjected to partial liver resection. Specifically, subjects classified as "no-risk" are also subjected to partial liver resection without prior stimulation of liver regeneration. Specifically, subjects classified as "medium-risk" are subject to partial liver resection, but first they are subjected to treatment aiming to stimulate liver regeneration. Preferably, following stimulation of liver regeneration regeneration-success is assessed and the subject's risk of developing liver dysfunction after partial liver resection is determined before the subject is subjected to partial liver resection.

Specifically, subjects classified as "medium-risk" are subjected to treatment before partial liver resection, which treatment is selected from the group consisting of neoadjuvant chemotherapy, portal vein embolization, associating liver partition and portal vein ligation for staged hepatectomy (ALPPS), exercise intervention ("prehabilitation") or pharmacological therapy reducing portal vein hypertension. Specifically, exercise intervention and/or diet changes can aid in liver regeneration by improvement of overall fitness and health. Specifically, a further option for subjects classified as medium-risk is a modified surgical strategy. Preferably, in said modified surgical strategy, the necessary size of the resected liver portion is reduced by combination with thermic ablation of tumor centers.

Specifically, miRNA signatures described herein are used to determine a time-point for partial liver resection at which the patient's risk of developing post-operative liver dysfunction is low. Specifically, samples of subjects that are classified as "medium-risk", and thus subjected to treatment such as ALPPS before liver resection, are provided at more than one time-point so that an optimal time-point for partial liver resection can be determined. Specifically, samples are provided and the risk of developing liver dysfunction is determined once every two weeks, once a week, daily or at least twice a day. Specifically, once the sample is classified as "low-risk", the time-point for partial liver resection is optimal.

Specifically, subjects classified as "high-risk" are not subjected to partial liver resection. Specifically, said subjects are instead subjected to liver transplantation, palliative chemotherapy, radiofrequency ablation, or transarterial chemoembolisation (TACE). Specifically, said treatment is selected in dependence of the tumor load.

Herein further provided is an in vitro method of monitoring regeneration-success of liver regeneration stimulation of a subject, comprising the steps of
 a) providing a sample from said subject,
 b) determining the expression level ratios of miR-151a to miR-192 and of miR-122 to miR-151a in said sample,
 c) determining the expression level ratios of miR-151a to miR-192 and of miR-122 to miR-151a in a reference sample, wherein the reference sample is an earlier sample of the subject,
 d) comparing the expression level ratios of b) with the expression level ratios of c), and
 e) classifying the sample of said subject from the outcome of the comparison of step d) into one of two categories, "regeneration-success" or "no regeneration-success".

Specifically, the liver regeneration stimulation whose regeneration-success is to be determined according to the in vitro method provided herein is selected from the group consisting of induction of liver hypertrophy by portal vein embolization, induction of liver hypertrophy by associating liver partition and portal vein ligation for staged hepatectomy (ALPPS), exercise intervention ("prehabilitation") to improve overall fitness, and pharmacological therapy reducing portal vein hypertension.

Specifically, the subject is suffering from malignant lesions in the liver, preferably metastatic colorectal cancer, hepatocellular carcinoma or cholangiocellular carcinoma, or from benign liver tumors, hepatic cysts and/or parasites. Specifically, the subject is suffering from one or more tumors, benign or malignant, in the liver. The tumors can originate from any tissue or organ.

According to a specific embodiment, the sample is selected from the group consisting of blood, serum, plasma, specifically platelet-poor plasma, lymph, urine and saliva and biopsy probes. Specifically, the sample is cell-free blood.

According to a further specific embodiment, the expression levels or expression level ratios of the sample are compared with the reference expression levels or expression level ratios using a classification model.

Specifically, a classification model classifies the sample of a subject from the outcome of the comparison with the reference into one of the at least two classes.

Specifically, the classification model is selected from the group consisting of logistic regression models, support vector machine models and decision tree models.

Further described herein are clinically useful cut-offs predicting risk of liver dysfunction, in particular following partial liver resection. Specifically, a low stringency cut-off with a Probability Score of less than 0.59, specifically less than 0.58, 0.57, 0.56, 0.55, 0.54, 0.53, 0.52, 051 or 0.50 identifies subjects at low risk of developing liver dysfunction and patients that can undergo partial liver resection with low risk. Preferably, a Probability Score of less than 0.58 (P<0.58) classifies a patient as low-risk. Specifically, a stringent cut-off with a probability score of more than 0.58, specifically more than 0.59, 0.60, 0.61, 0.62, 0.63, 0.64 or 0.65 identifies patients with medium risk of developing liver dysfunction, such patients should be optimized prior to surgery. Preferably, a Probability Score of more than 0.58 (P>0.58) classifies a patient as medium-risk. Probability Scores of higher than 0.66, 0.67, 0.68, 0.69, 0.70, 0.71, 0.72, 0.73, 0.74 or 0.75 identify subjects as high-risk patients, who preferably should not undergo surgical partial liver resection. Preferably, a Probability Score of higher than 0.68 (P>0.68) identifies subjects at high-risk of developing liver dysfunction.

According to a specific embodiment, the expression levels are determined using a method selected from the group consisting of a sequencing-based method, specifically next-generation sequencing, an array-based method and a PCR-based method, specifically a quantitative PCR-based method.

Specifically, the difference in miRNA levels is determined by quantitative or digital PCR, DNA/RNA sequencing, specifically Next-Generation Sequencing, microarray, Luminex™ luminescence based nucleic acid assays, or other hybridization-based techniques.

Herein further provided is a kit-of-parts comprising
a) detection reagents capable of detecting the expression level of at least one microRNA, selected from the group consisting of miR-151a, miR-192 and miR-122, in a subject's sample,
b) reference expression levels,
software comprising the classification models for comparison of expression levels of a) with expression levels of b) and for classification of the subject's sample into one of at least two classes, wherein each class is one of the at least two categories "high-risk" and "low-risk" of liver dysfunction after partial liver resection.

FIGURES

FIG. 1: Differences in pre-surgical microRNA patterns in patients undergoing liver resection. Volcano plot of differentially regulated microRNAs in pre-surgical plasma of patients with liver dysfunction. To identify biomarker candidates' cut-offs for plasma concentration (average log 2 counts per million (logCPM)>5), effect size (fold change>1.3) and significance level (raw p<0.2) were implied. A set of 19 microRNA, of which 12 were up-regulated (red) and 7 down-regulated (blue) was identified.

FIG. 2: Analysis of the diagnostic performance of miRNA pairs to predict liver dysfunction. (A) Importance of miRNA pairs in a random forest classification model (most important ones are at the top with highest mean decrease accuracy). (B) Distribution of ratios measured by qPCR in the discovery cohort for miR151a-5p_192-5p (boxplots and p-values from two sided Wilcoxon rank-sum test) and (C) for miR122-5p_151a-5p. (D) ROC curves for a logistic regression model including miR122-5p_151a-5p in the discovery cohort (results from leave-one-out cross validation are in grey) and (E) a logistic regression model including miR151-5p_192-5p, and (F) a logistic regression model including both miRNA pairs. (G, H) The performance is described by the area under curve (AUC) and whether the classification deviate significantly from the random assignment (AUC=0.5) is indicated by the p-value. The percentage of true postoperative LD on predicted controls and predicted LD were analysed for both model defined cut-offs P>0.59 and P>0.68.

FIG. 3: The predictive performance of the top two miRNA ratios was validated in an independent study of post-operative LD. MiRNAs were analyzed by RT-qPCR in 24 subjects of which 5 (16.7%) experienced the adverse outcome post-surgery. Pre-operative regulation of miRNA pairs 122-5p/151a-5p (A) and 151a-5p/192-5p (B) was observed in plasma. (C) The predictive performance of the previously defined multivariate logistic prediction models was validated using ROC analyses. The performance is described by the area under curve (AUC) and whether the classification deviate significantly from the random assignment (AUC=0.5) is indicated by the p-value. The percentage of true postoperative LD on predicted controls and predicted LD were analysed for both model defined cut-offs P>0.59 and P>0.68 (D, E).

FIG. 4: Performance evaluation of microRNA model on the basis of the complete dataset. Two cut-offs (low stringency, P=0.59; and high stringency, P=0.68) for the logistic regression model output were analyzed for their performance to predict post-operative liver dysfunction. Performance was described using sensitivity (SN), specificity (SP), positive predictive value (PPV), negative predictive value (NPV) and the odds ratio (OR), which is the ratio of odds of suffering from post-operative liver dysfunction associated with a positive test results compared to a negative test result. The low stringency cut-off (P=0.59) yielded balanced PPV and NPV values (0.80 and 0.81, respectively), while the stringent cut-off (P=0.68) resulted in a perfect PPV of 1.0, with an acceptable NPV of 0.74 (A). This means that 100% of the patients who tested positive suffered from post-operative LD, while 74% who were tested negative did not suffer from post-operative LD. Vice-versa, 26% who were tested negative did in fact suffer from post-operative LD (see panel A). The ORs for an adverse event were 15.92 (p<0.0001) and infinite (p<0.0001), respectively. Receiver operator characteristic (ROC) curve analysis was performed for the microRNA model to compare its performance against that of standard liver function parameters (B). ORs for other adverse post-operative outcomes were analyzed for both model cut-offs: severe morbidity (C) and mortality (D). Postoperative ICU stay (E,) and hospitalization (F) were significantly prolonged in our predicted risk groups (boxplots are shown without outliers; p-values from two sided Wilcoxon rank-sum test). ALT, alanine transaminase; AST, aspartate transaminase; GGT, gamma-glutamyltransferase: ICG-PDR, indocyanine green (ICG) plasma disappearance rate; ICG R15 ICG-retention rate at 15 min, ICU, intensive care unit.

Figure 5B:
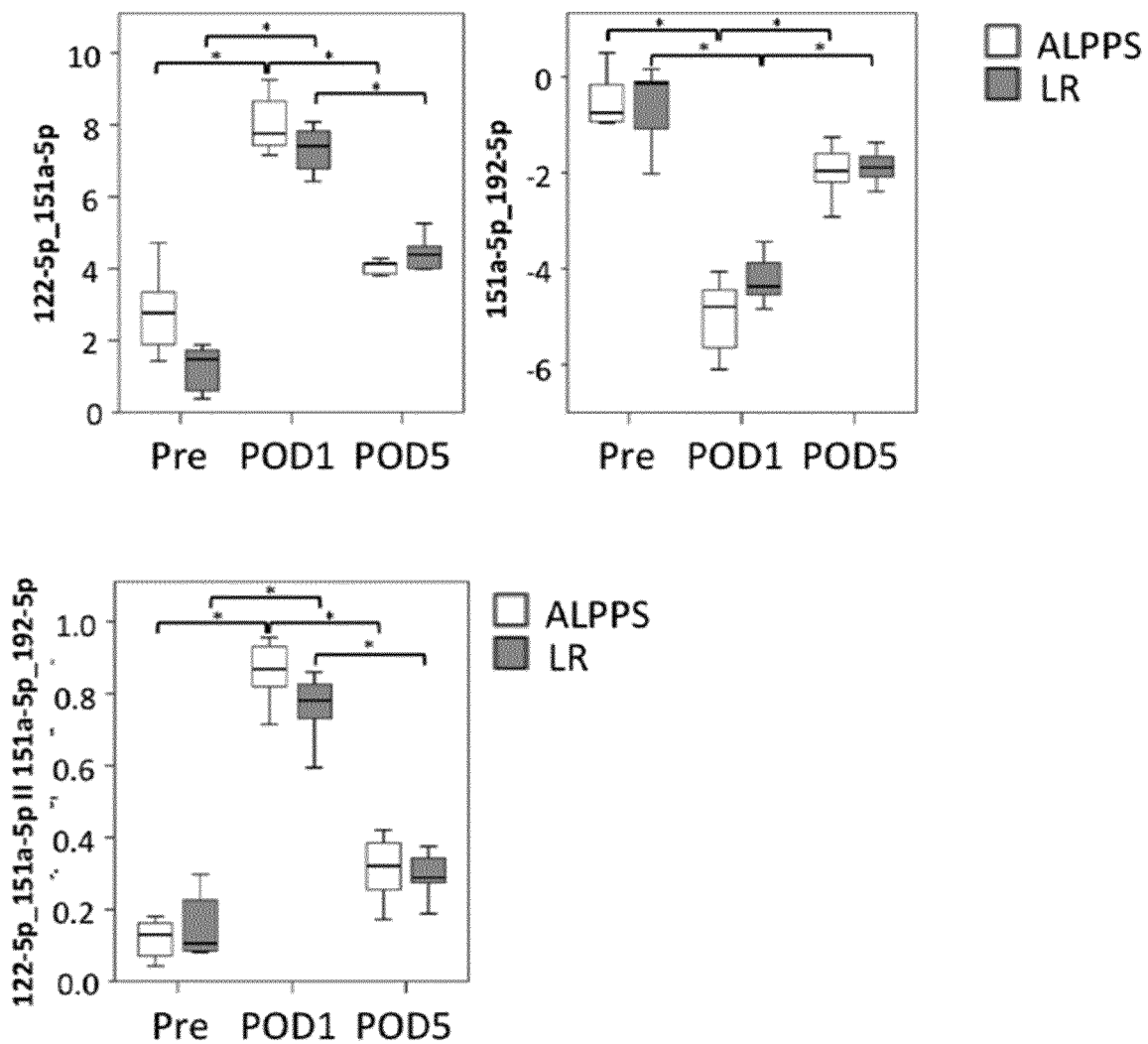
Figure 5C:
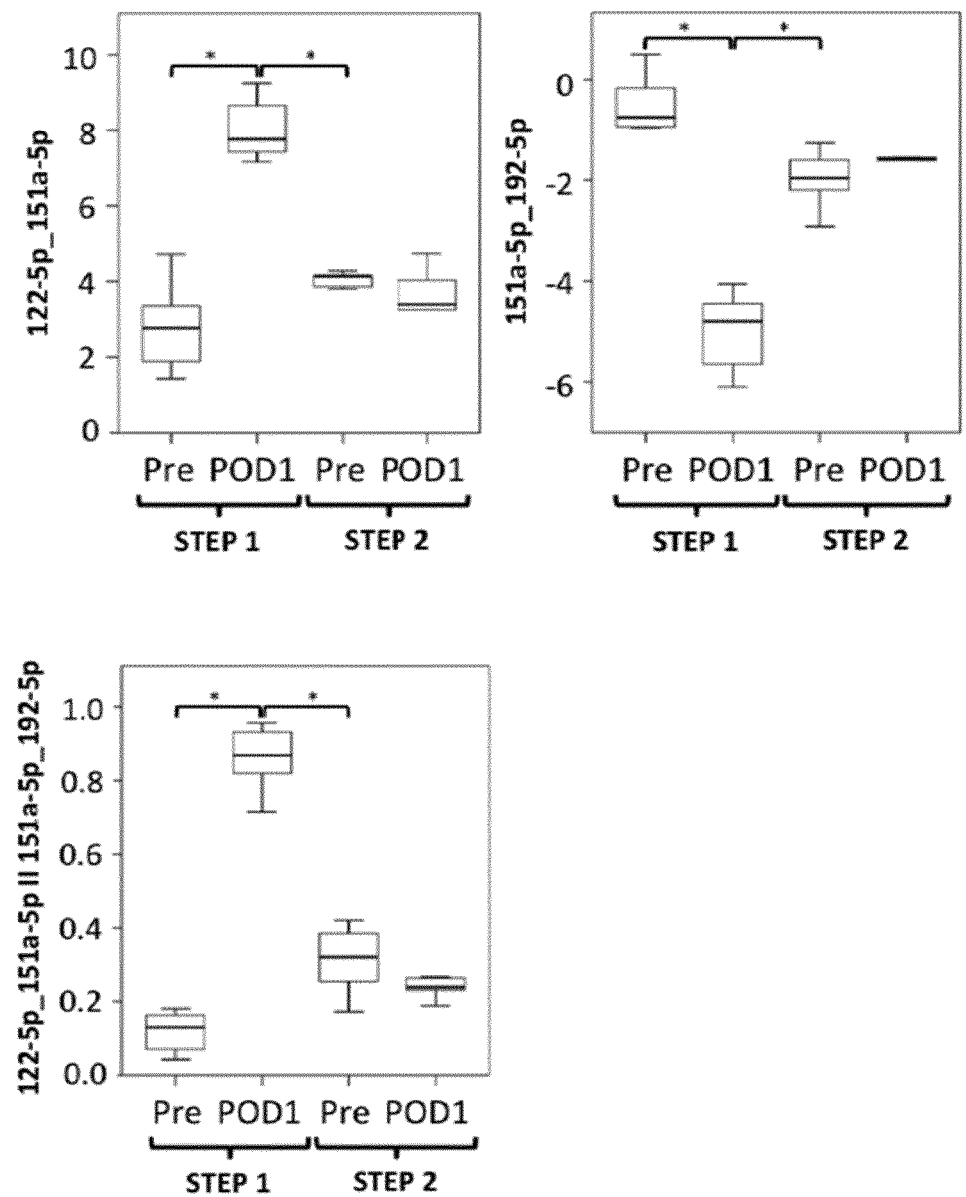

FIG. 5: MiRNA pairs follow liver function recovery after partial hepatectomy and predict postoperative LD after the second step of ALPPS. (A) illustrates the study design of this additional exploratory study as well as summarizes the procedural algorithm of ALPPS. The ALPPS procedure was first described by Schnitzbauer et al. and has been developed to allow for rapid liver regeneration in borderline resectable patients with an insufficient liver remnant. Briefly, during the first step of the ALPPS procedure the portal vein branch, feeding the tumor bearing liver lobe, is selectively ligated, while the arterial as well as bile structures are preserved and the liver parenchyma is further transsected during this initial step of surgery. This procedure leads to an improved liver regeneration within the time frame of days. Still, after this substantial gain of liver regeneration a second surgical procedure has to be performed in which the ligated remaining liver lobes need to be removed. Perioperative dynamics of miRNAs were evaluated in a group of 7 patients with regular partial hepatectomy and 8 ALPPS patients (details are listed in table 3) for which longitudinal measurement of miRNAs could be performed on the basis of repeatedly collected plasma samples. Time points of blood collection are given in (A). Perioperative dynamics of miRNA pairs as well as combined pairs are illustrated in (B). As during the second step of ALPPS only the atrophic liver lobe is removed miRNA pairs were further analyzed after the second step of ALPPS as illustrated in (C), showing an almost vanished increase in miRNA ratios after this second operation. Ultimately, (D) illustrates the predictive potential of the combined miRNA pairs prior to the second step of ALLPS as stratified according to postoperative LD and mortality after the removal of the atrophic lobe. * P<0.05, ** P<0.005.

DETAILED DESCRIPTION

Postoperative liver dysfunction (LD) as a result of insufficient hepatic regeneration occurs in up to 30% of patients undergoing major hepatic resection, which concomitantly increases patient morbidity and mortality. Still, treatment options as well as reliable predictive biomarkers to determine patients at risk to develop LD after surgery are limited. Accordingly, there is an urgent need for an easily assessable preoperative test to predict postoperative liver function recovery, specifically as current markers are often expensive, time consuming and sometimes invasive. microRNA (miRNA) signatures represent potent diagnostic, prognostic and treatment response biomarkers for several diseases.

Circulating microRNAs in cell-free blood such as serum or plasma are a minimal or non-invasive source of biomarkers allowing minimal-invasive detection and therefore a broad applicability in clinics and research repositories.

The term "sample" generally refers to tissue or organ sample, blood, cell-free blood such as serum and plasma, platelet-poor plasma, lymph, urine, saliva and biopsy probes. Preferably, the sample is a plasma sample.

According to a specific embodiment, the sample used herein is platelet-poor plasma, which has undergone two centrifugation steps during the collection process. Specifically, the first centrifugation step is performed at lower speed, for example about 1.000 g-forces (g), while the second centrifugation step is performed at a high speed, for example about 10.000 g. Such centrifugation helps to ensure complete removal of platelets and larger extracellular vesicles such as apoptotic bodies, which could interfere with the measurement of microRNAs The preferred type of anti-coagulant that is used to prevent platelet activation is CTAD (Sodium-Citrate, Theophyllin, adenosine, dipyridamole). Specifically, CTAD, Sodium-citrate or Potassium-EDTA (K2-EDTA) can be used to prevent platelet activation.

Specifically, the platelet-poor plasma is essentially free of platelets and medium and larger extracellular vesicles, which pellet at centrifugation speeds below 20,000 g.

The term "cell-free" as used herein refers to a sample that lacks any cells to an extent of about 90%.

As used herein, the term "subject" or "individual" or "patient" shall refer to a warm-blooded mammalian, particularly a human being.

The term "patient" includes human and other mammalian subjects that receive either prophylactic or therapeutic treatment or are diagnosed of a specific disease, like, but not limited to, hepatic cancer or metastatic colorectal cancer.

The term "treatment" is thus meant to include both prophylactic and therapeutic treatment.

As used herein, the term "cohort of individuals" or "pool of individuals" shall refer to a group of healthy individuals and may specifically refer to the samples received from said individuals. The number of individuals of a cohort can vary, i.e. it may comprise 2, 3, 4, 5, 6, 7 or more individuals, however it also may be a larger group of subjects, like for example but not limited to at least 10, 25, 50, 100 or more individuals. According to the embodiment of the invention the cohort may also comprise large cohorts of 500 or more individuals.

As used herein, the term "about" encompasses the explicitly recited values as well as small deviations therefrom. Accordingly, a deviation from a recited value for 10%, preferably 5%, preferably 1% is encompassed by the term "about".

The term "microRNA signature" refers to specific microRNA expression profiles representing potent and robust diagnostic, prognostic and treatment response biomarkers. As used herein, the term "microRNA signature" or "miRNA signature" refers to differences in the expression profile of circulating miRNAs between patients with and without liver dysfunction after partial liver resection. Specifically, the miRNA signature described herein comprises at least one of the microRNAs miR-151a, miR-122 and miR-192.

The term "in vitro method" as used herein refers to methods performed outside of a living organism. Specifically, it refers to methods performed on samples such as isolated tissues, organs or cells, preferably blood, even more preferably plasma. Such in vitro method is therefore not performed on the living organism; it is particularly not performed on humans.

The term "liver dysfunction", synonymously used with "LD" or "hepatic dysfunction" refers to a malfunctioning of the liver, which may manifest as an acute or chronic sub-clinical cellular disturbance but can progress to life-threatening hepatic failure with multiple organ system compromise. Perioperative morbidity and mortality can be significant; hepatic function (glucose homeostasis, protein and procoagulant synthesis, bilirubin metabolism, and biotransformation of drugs and endogenous toxins) may all be impaired. The degree of impairment and the severity of extrahepatic involvement can be variable. Insufficient hepatic regeneration after liver resection was shown to result in postoperative LD, which occurs in up to 30% of patients after major hepatic resections. Hence, risk stratification for optimized patient selection prior to liver surgery is key for minimizing the incidence of postoperative LD and concomitant complications. Subjects identified as being at an increased of postoperative LD can be subjected to treatments aiding in liver regeneration prior to surgery or their postoperative care can be adjusted to cope with the increased risk of LD. Adjustment of postoperative care can for example mean a longer stay in the intensive care unit to allow close supervision of the subjects liver function.

The term "partial liver resection" or "partial hepatectomy" refers to the surgical removal of a part of the liver. Most hepatectomies are performed for the treatment of hepatic neoplasms, benign or malignant. Benign neoplasms include hepatocellular adenoma, hepatic hemangioma and focal nodular hyperplasia. The most common malignant neoplasms (cancers) of the liver are metastases; those arising from colorectal cancer are among the most common, and the most amenable to surgical resection. The most common primary malignant tumor of the liver is the hepatocellular carcinoma. Hepatectomy may also be the procedure of choice to treat intrahepatic gallstones and hepatic or parasitic cysts of the liver.

Primary liver cancer, also known as hepatic cancer and primary hepatic cancer, is cancer that starts in the liver. Cancer which has spread from elsewhere to the liver, known as liver metastasis or secondary liver cancer, is more common than that which starts in the liver. The term "malignant lesions in the liver" as used herein, refers to both primary and secondary liver cancer. The most frequent liver cancer, accounting for approximately 75% of all primary liver cancers, is hepatocellular carcinoma (HCC) (also named hepatoma, which is a misnomer because adenomas are usually benign). HCC is a cancer formed by liver cells, known as hepatocytes, which become malignant. Another type of cancer formed by liver cells is hepatoblastoma, which is specifically formed by immature liver cells. It is a rare malignant tumor that primarily develops in children, and accounts for approximately 1% of all cancers in children and 79% of all primary liver cancers under the age of 15. Most hepatoblastomas form in the right lobe. Liver cancer can also form from other structures within the liver such as the bile duct, blood vessels and immune cells. Cancer of the bile duct (cholangiocarcinoma and cholangiocellular cystadenocarcinoma) accounts for approximately 6% of primary liver cancers. There is also a variant type of HCC that consists of both HCC and cholangiocarcinoma. Tumors of the blood vessels (angiosarcoma and hemangioendothelioma, embryonal sarcoma and fibrosarcoma are produced from a type of connective tissue known as mesenchyme. Cancers produced from muscle in the liver are leiomyosarcoma and rhabdomyosarcoma. Other less common liver cancers include carcinosarcomas, teratomas, yolk sac tumours, carcinoid tumours and lymphomas. Lymphomas usually have diffuse infiltration to liver, but may also form a liver mass in rare occasions.

Many cancers found in the liver are not true liver cancers, but are cancers from other sites in the body that have spread to the liver (secondary liver cancer). Frequently, the site of origin is the gastrointestinal tract, since the liver is close to many of these metabolically active, blood-rich organs near to blood vessels and lymph nodes (such as pancreatic cancer, stomach cancer, colon cancer and carcinoid tumors mainly of the appendix). Secondary liver cancer may also originate from breast cancer, ovarian cancer, lung cancer, renal cancer, prostate cancer.

The leading cause of liver cancer is cirrhosis due to hepatitis B, hepatitis C, or alcohol. Other causes include aflatoxin, non-alcoholic fatty liver disease, and liver flukes. The most common types are hepatocellular carcinoma (HCC), which makes up 80% of cases, and cholangiocarcinoma. Less common types include mucinous cystic neoplasm and intraductal papillary biliary neoplasm.

According to the method provided herein the treatment strategy of patients suffering from liver lesions can be selected. Subjects whose sample is classified into the category no-risk or low-risk are good candidates for partial liver resection, as their risk of developing liver dysfunction after partial liver resection is low. Said subjects can be subjected to partial liver resection directly following assessment of LD risk or subjected to liver regeneration stimulation prior to partial liver resection.

Specifically, subjects whose sample is classified as medium-risk or high-risk are not subjected to partial liver resection directly following assessment of LD risk. Preferably, subjects classified as medium-risk are subjected to therapy, surgical or pharmacological or other, aiding in liver regeneration. Said therapy can be neoadjuvant chemotherapy, portal vein embolization, associating liver partition and portal vein ligation for staged hepatectomy (ALPPS), exercise intervention ("prehabilitation") or pharmacological therapy reducing portal vein hypertension. Specifically, regeneration-success of said therapy can be monitored by the method provided herein.

Preferably, subjects whose sample is classified as belonging to the high-risk category are not subjected to partial liver resection. Preferably, high-risk subjects are subjected to liver transplantation, palliative chemotherapy, radiofrequency ablation or transarterial chemoembolization (TACE).

Specifically, a subject's risk of developing liver dysfunction, in particular after partial liver resection, can be assessed repeatedly according to the method provided herein.

The term "regeneration-success" as used herein is defined as improving liver function and decreasing the risk of liver dysfunction after partial liver resection. Hence, a marker that monitors liver regeneration should be preferentially related to the clinical outcome for a patient, i.e. the reduction in risk of liver dysfunction. Moderate regeneration success reduces liver dysfunction risk by about 25% up to about 50%. High regeneration success results in a risk reduction by more than 50%. No reduction in the risk of developing liver dysfunction and/or no improvement of liver function is indicative of no regeneration success. Specifically, liver function can be assessed using liver function tests known in the art, such as for example tests detecting prothrombin time (PT/INR), aPTT, albumin and bilirubin (direct and indirect).

Specifically, regeneration-success is monitored by an in vitro method comprising the sequential steps of:
a) providing a sample from said subject,
b) determining the expression level ratios of miR-151a to miR-192 and of miR-122 to miR-151a in said sample,
c) determining the expression level ratios of miR-151a to miR-192 and of miR-122 to miR-151a in a reference sample, wherein the reference sample is an earlier sample of the subject,
d) comparing the expression level ratios of b) with the expression level ratios of c), and
e) classifying the sample of said subject from the outcome of the comparison of step d) into one of two categories, "regeneration-success" or "no regeneration-success".

The present invention provides selected miRNAs for use in a method for the prediction of liver dysfunction after partial liver resection and for the monitoring of liver function following partial liver resection or liver regeneration stimulation or for monitoring the treatment in subjects undergoing therapy, specifically treatment reducing the hepatic tumor load.

Specifically, said miRNAs are miR-151a, miR-122 and/or miR-192 or isoforms or variants thereof. Preferably, said miRNAs are hsa-miR-151a-5p, hsa-miR-122-5p and/or hsa-miR-192-5p or isoforms or variants thereof.

The detection of an increase or decrease of the level of one or more of said miRNAs compared to the level in subjects without liver dysfunction can be used for predicting the risk of developing liver dysfunction in a subject.

Specifically, measuring a decrease in the level of hsa-miR-151a-5p, or isoforms or variants thereof, and/or an increase in the level of hsa-miR-192-5p or hsa-miR-122-5p, or isoforms or variants thereof, can be a specific indicator for an increased risk of developing liver dysfunction. Said increase or decrease of miRNAs is specifically based on data derived from blood or serum levels in subjects who developed liver dysfunction after partial liver resection.

Further described herein are clinically useful cut-offs predicting risk of liver dysfunction, in particular following partial liver resection. Specifically, a low stringency cut-off with a Probability Score of less than 0.59, specifically less than 0.58, 0.57, 0.56, 0.55, 0.54, 0.53, 0.52, 051 or 0.50 identifies subjects at low risk of developing liver dysfunction and patients that can undergo partial liver resection with low risk. Preferably, a Probability Score of less than 0.58 (P<0.58) classifies a patient as low-risk. Specifically, a stringent cut-off with a probability score of more than 0.58, specifically more than 0.59, 0.60, 0.61, 0.62, 0.63, 0.64 or 0.65 identifies patients with medium risk of developing liver dysfunction, such patients should be optimized prior to surgery. Preferably, a Probability Score of more than 0.58 (P>0.58) classifies a patient as medium-risk. Probability Scores of higher than 0.66, 0.67, 0.68, 0.69, 0.70, 0.71, 0.72, 0.73, 0.74 or 0.75 identify subjects as high-risk patients, who preferably should not undergo surgical partial liver resection. Preferably, a Probability Score of higher than 0.68 (P>0.68) identifies subjects at high-risk of developing liver dysfunction.

Surprisingly, using the method as described herein, 100% of patients with a Probability Score of higher than 0.68 developed liver dysfunction after partial liver resection. Whereas only 80% of the patients with a Probability Score of higher than 0.59 developed liver dysfunction and about 80% of subjects with a Probability Score lower than 0.59 did not develop liver dysfunction.

Specifically, increased risk of developing liver dysfunction after partial liver resection can be determined measuring expression level ratios between pairs of micro RNAs selected from the group consisting of miR-151a, miR-122 and miR-192. Specifically, for a pair of microRNAs (miR1, miR2) the $\log_2$ ratios of expression values $\log_2$ (miR1/miR2) were calculated by difference in their Cq values ($\Delta Cq = Cq_{miR2} - Cq_{miR1}$). Specifically, to compare results for microRNA pairs from NGS analyses (log 2 fold change) with results from qPCR analyses ($\Delta Cq$) linear regression analyses can be performed. Specifically, linear association can be tested by a two-sided Wald test for the respective coefficient and the coefficient of determination can be calculated. Distribution and differences of $\Delta Cq$ values between the subject's sample and the reference sample can be tested using a two-sided Wilcoxon rank-sum test.

As used herein, the term "microRNA" or "miRNA" or "miR" designates a non-coding RNA molecule of between 17 and 25 nucleotides which hybridizes to and regulates the expression of a coding messenger RNA. The term "miRNA molecule" refers to any nucleic acid molecule representing the miRNA, including natural miRNA molecules, i.e. the mature miRNA, pre-miRNA, pri-miRNA.

"miR precursor", "pre-miRNA" or "pre-miR" designates a non-coding RNA having a hairpin structure, which contains a miRNA. A pre-miRNA is the product of cleavage of a primary mi-RNA transcript, or "pri-miR" by the double-stranded RNA-specific ribonuclease known as Drosha. The precursors may be forms of the respective polynucleotides as they occur during maturation of the respective polynucleotides. Specifically, examples of said precursors are listed in Table 1, specifically they are of SEQ ID Nos. 4 to 6.

TABLE 1 miRNA SEQ IDs

| mature ID | mature Sequence | SEQ ID | mature miRNA Accession | precursor -miRNA | precursor Sequence | SEQ ID | precursor miRNA Accession |
|---|---|---|---|---|---|---|---|
| hsa-miR-122-5p | UGGAG UGUGA CAAUG GUGUU UG | 1 | MIMAT0000421 | hsa-miR-122 | CCUUAGCAGAGC UGUGGAGUGUGA CAAUGGUGUUUG UGUCUAAACUAU CAAACGCCAUUAU CACACUAAAUAGC UACUGCUAGGC | 4 | MI0000442 |
| hsa-miR-192-5p | CUGAC CUAUG AAUUG ACAGC C | 2 | MIMAT0000222 | hsa-miR-192 | GCCGAGACCGAG UGCACAGGGCUC UGACCUAUGAAU UGACAGCCAGUG CUCUCGUCUCCC CUCUGGCUGCCA AUUCCAUAGGUC ACAGGUAUGUUC GCCUCAAUGCCA GC | 5 | MI0000234 |
| hsa-miR-151a-5p | UCGAG GAGCU CACAG UCUAG U | 3 | MIMAT0004697 | hsa-miR-151a | UUUCCUGCCCUC GAGGAGCUCACA GUCUAGUAUGUC UCAUCCCUACU AGACUGAAGCUC CUUGAGGACAGG GAUGGUCAUACU CACCUC | 6 | MI0000809 |

Specifically, for classification of a subject's sample into one of the categories no-risk, low-risk, medium-risk and high-risk or regeneration-success and no regeneration-success each of the two micro RNA pairs are included in a univariate and multivariate logistic regression model. Specifically, a leave-one-out cross validation strategy can be applied, and if applied, evaluated by a receiver operating characteristics (ROC) analysis.

Specifically, to identify optimal (clinically relevant) classification cutoffs, contingency tables (TP,FP;FN,TN) and associated parameters such as sensitivity (SN), specificity (SP), positive prediction value (PPV), negative prediction value (NPV), accuracy (ACC), F1-score (F1) and Matthews correlation coefficient (MCC) can be used. Cutoffs can be calculated based on the multivariate logistic regression model including the 2 micro RNA pairs. Preferably, the cutoffs maximal MCC and PPV=1 (false positives FP=0) are used.

Nucleotide sequences of mature miRNAs (SEQ ID Nos 1 to 3) and their respective precursors are known in the art and available from the database miRBase at mirbase.org/index.shtml or from Sanger database at microrna.sanger.ac.uk/sequences/ftp.shtml. The nucleotide sequences are also specifically disclosed in table 1 including reference to the respective miRBase accession number.

Identical polynucleotides as used herein in the context of a polynucleotide to be detected in context of the present invention may have a nucleic acid sequence with an identity of at least 90%, 95%, 97%, 98% or 99% to a polynucleotide comprising or consisting of the nucleotide sequence of any one of SEQ ID Nos. 1 to 3. Specifically, the sequences of identical polynucleotides differ from the sequences in table 1 in no more than 1, 2 or 3 nucleotides.

Furthermore, identical polynucleotides as used herein in the context of a polynucleotide to be detected in context of the present invention may have a nucleic acid sequence with an identity of at least 90%, 95%, 97%, 98% or 99% to a polynucleotide comprising or consisting of the nucleotide sequence of any one of SEQ ID Nos. 4 to 6 including one, two, three or more nucleotides of the corresponding pre-miRNA sequence at the 5'end and/or the 3'end of the respective seed sequence.

For the purpose of the invention, "isoforms and variants" (which have also be termed "isomiRs") of a reference miRNA include trimming variants (5' trimming variants in which the 5' dicing site is upstream or downstream from the reference miRNA sequence; 3' trimming variants: the 3' dicing site is upstream or downstream from the reference miRNA sequence), or variants having one or more nucleotide modifications (3' nucleotide addition to the 3' end of the reference miRNA; nucleotide substitution by changing nucleotides from the miRNA precursor), or the complementary mature microRNA strand including its isoforms and variants (for example for a given 5' mature microRNA the complementary 3' mature microRNA and vice-versa). With regard to nucleotide modification, the nucleotides relevant for RNA/RNA binding, i.e. the 5'-seed region and nucleotides at the cleavage/anchor side are exempt from modification.

As used herein, if not otherwise stated, the term "miRNA" encompasses 3p and 5p strands and also its isoforms and variants.

Specifically, the term "miR-respective-number-5p" as used herein in the specification also encompasses its complementary 3p miRNA and vice versa.

In specific embodiments, the miRNAs of interest are detected using a nucleotide that hybridizes, preferably under stringent conditions, with said miRNA of interest and measuring the hybridization signal.

In a preferred embodiment, the level of miRNAs of interest is determined by next-generation sequencing. The term "next-generation sequencing" (NGS), also known as high-throughput sequencing, is used herein to describe a number of different modern sequencing technologies that allow to sequence and quantify levels of DNA and RNA much more quickly and cheaply than the previously used sequencing methods such as Sanger sequencing. It is based on micro- and nanotechnologies to reduce the size of sample, the reagent costs, and to enable massively parallel sequencing reactions. It can be highly multiplexed which allows simultaneous sequencing and analysis of millions of samples. NGS includes first, second, third as well as subsequent Next Generations Sequencing technologies. Non limiting examples are the nanopore or semiconductor technologies (e.g. Oxford Nanopore Technologies, United Kingdom) or the Illumine smallRNA-Seq Platform (Luo S., 2012, Methods Mol Biol. 822: 183-8) or electron detection-based methods such as Thermo Fisher's Ion Torrent.

Specifically, NGS refers to a high-throughput sequencing technology that performs thousands or millions of sequencing reactions in parallel. Although the different NGS platforms use varying assay chemistries, they all generate sequence data from a large number of sequencing reactions running simultaneously on a large number of templates, where the number of sequences derived from a specific DNA or RNA, specifically miRNA, correlates with the RNA level in a biologic sample. Typically, the sequence data is collected using a scanner, and then assembled and analyzed bioinformatically. Thus, the sequencing reactions are performed, read, assembled, and analyzed in parallel; see, e.g. Behjati S and Tarpey, P., 2013 (Arch. Di. Child Educ Pract Ed 2013, 98, 236-238); Head S. et al., 2015 (Biotechniques, 56(2), 61-passim).

Some NGS methods require template amplification and some do not. Amplification requiring methods include pyrosequencing (e.g., U.S. Pat. No. 6,258,568; commercialized by Roche); the Solexa/Illumina platform (e.g., U.S. Pat. Nos. 6,833,246, 7,115,400, and 6,969,488); and the Supported Oligonucleotide Ligation and Detection (SOLiD) platform (Applied Biosystems; e.g., U.S. Pat. Nos. 5,912,148 and 6,130,073). Methods that do not require amplification, e.g., single-molecule sequencing methods, include nanopore sequencing, HeliScope (U.S. Pat. Nos. 7,169,560; 7,282,337; 7,482,120; 7,501,245; 6,818,395; 6,911,345; and 7,501,245); real-time sequencing by synthesis (see, e.g., U.S. Pat. No. 7,329,492); single molecule real time (SMRT) DNA sequencing methods using zero-mode waveguides (ZMWs); and other methods, including those described in U.S. Pat. Nos. 7,170,050; 7,302,146; 7,313,308; and 7,476,503, US 20130274147; US20140038831, and Metzker, Nat Rev Genet 11(1): 31-46 (2010). Alternatively, hybridization-based sequence methods or other high-throughput methods can also be used, e.g., microarray analysis, NANOSTRING, ILLUMINA, or other sequencing platforms.

Specifically, small RNA sequencing libraries can be generated using library preparation kits well known in the art, such as the CleanTag SmallRNA library preparation kit (TriLink, USA). Usually, RNA is first reverse transcribed into DNA followed by PCR amplification. PCR amplification can be performed using barcoded primers, such as the barcoded primers from Illumina for small RNA sequencing. Before sequencing, PCR products are purified using protocols well known in the art. For example, PCR products can be purified using the QiaQuick protocol from Qiagen and can subsequently be size checked by suitable methods, such as e.g. capillary electrophoresis.

Specifically, next-generation sequencing can be performed on any suitable platform, such as e.g. the Illumina NextSeq 500. Sequencing reads are usually adapter-trimmed, quality checked and edited according to bioinformatics methods well known in the art to prepare for further use.

In a further preferred embodiment, the level of the miRNAs of interest is determined by polymerase chain reaction (PCR). PCR methods are well known in the art and widely used. They include quantitative real time PCR, semi-quantitative PCR, multiplex PCR, digital PCR, or any combination thereof. In a particularly preferred embodiment, the levels of miRNAs are determined by quantitative real time PCR (qRT-PCR). Methods of determining the levels of miRNAs using qRT-PCR are known in the art, and are usually preceded by reverse transcription of a miRNA into a cDNA.

In the PCR methods useful in the present invention, the primers are usually based on the mature miRNA molecule, but may include chemical modifications to optimize hybridization behavior.

qRT-PCR methods may determine an absolute level of expression of a miRNA. Alternatively, qRT-PCR methods may determine the relative quantity of a miRNA. The relative quantity of a miRNA may be determined by normalizing the level of the miRNA to the level of one or more internal standard nucleic acid sequences. In general, such internal standard nucleic acid sequences should have a constant level in the analyzed blood or serum sample. For instance, internal standard nucleic acid sequences may be constitutively transcribed RNA nucleic acid sequences such as mRNAs like glyceraldehyde-3-phosphate-dehydrogenase (GAPDH), beta-actin (ACTB), or non-coding RNAs such as 5S and 18S ribosomal RNA, RNU48, RNU44, and RNU6. In addition, miRNAs that have constant and high levels in serum or plasma, such as miR-23a-3p, miR-23b-3p, miR-15-5p or miR-16-5p can be used as references for relative quantification. In addition, synthetic RNA sequences added in an equimolar amount during RNA isolation or cDNA synthesis can be used as references for relative quantification of specific miRNAs.

Alternatively, the relative logarithmic difference between two miRNAs can be calculated to form self-normalizing miRNA pairs. Thereby the need for reference miRNAs can be circumvented.

An overview of real time PCR quantification methods useful in the present invention is given by Schmittgen et al., 2008, Methods. January; 44(1): 31-38.

Primers for detection of miRNAs are commercially available, e.g. as microRNA LNA™ PCR primer sets from Exiqon.

Since miRNAs are relatively short molecules, it may be useful to lengthen them by adding adenosine monomers to the strand (a technique known as polyadenylation) before reverse transcription and amplification. Briefly, the RNA may be extracted from the sample by a suitable reagent (e.g. Trizol reagent), polyadenylated in the presence of ATP and poly(A) polymerase, reverse transcribed into cDNA using a poly(T) adapter and 5' RACE sequence, and amplified using a forward primer derived from the 3' end of the miRNA and a reverse RACE primer. Improvements of this technique include designing the RACE primer with a nucleotide at its 3' end (constituting an A, C, or G, but not a T, so to exclude priming anywhere on the polyA sequence and enforce priming on the miRNA sequence) or RACE primers which are anchored at the 3' cDNA end of a specific microRNA using 2, 3, 4, or more nucleotides with or without chemical modification.

The detection of a miRNA may also be achieved by other methods known in the art, e.g. those described in WO2011/14476, like by the deep sequencing method, bead-based quantification, e.g. Illumina bead-arrays, hydrogel-particle based quantification, e.g. Firefly™, by microarray technology, e.g. the Ncode™ human miRNA array available from Invitrogen, chip arrays available from Affymetrix, Agilent, or microarrays which employ LNA-backbone capture probes (miRCURY LNA™ arrays), e.g., from Exiqon.

The difference in miRNA levels can also be determined using multiplex chemiluminescence-based nucleic acid assays such as Panomics, or reporter plasmid assays ("biosensors") containing reporter proteins with microRNA-complementary regulatory sites, or other hybridization-based techniques known in the art.

"Reference level", "reference ratio", "reference sample", "control" or "control sample" are terms which can be used interchangeably herein, and are to be understood as a sample or standard used for comparison with the experimental sample, i.e. the subject's sample whose risk for developing LD or regeneration-success is to be determined. The control may include a sample obtained from a healthy subject or a subject which did not develop liver dysfunction after partial liver resection. Additionally, a control may also be a standard reference value or range of values, i.e. such as stable expressed miRNAs in the samples, for example the endogenous control U6 snRNA.

The reference level can be determined as the average level of the corresponding miRNAs in a sample of a healthy subject, a subject which did not develop LD after partial liver resection and/or a subject after surgical, pharmacologic, dietary or life-style intervention. As an alternative, also a pool of samples may be used or a reference disclosed in literature.

The difference in miRNA levels can be determined by any of the methods described herein.

Specifically, the expression level or the expression level ratios of a sample can be compared with the reference expression level or expression level ratios using a classification model. A classification technique (or classifier) is a systematic approach to building classification models from an input data set, such as microRNA expression levels of patients with and without liver dysfunction after partial liver resection. Examples include logistic regression models, support vector machine models, decision tree models, rule-based classifiers, neural networks and naïve Bayes classifiers. Each technique employs a learning algorithm to identify a model that best fits the relationship between the attribute set and class label of the input data. The model generated by a learning algorithm should both fit the input data well and correctly predict the class labels of data it has never seen before. Therefore, a key objective of the learning algorithm is to build models with good generalization capability, i.e. models that accurately predict the class labels of previously unknown data.

A logistic regression model is estimating the parameters of a logistic model. A logistic model is one where the log-odds of the probability of an event is a linear combination of independent or predictor variables. It models probability of output in terms of input and can be used to make a classifier by choosing a cutoff value and classifying inputs with probability greater than the cutoff as one class and probability lower than the cutoff as the other.

Support vector machines (SVM) are supervised learning models with associated learning algorithms that analyze data used for classification and regression analysis. Given a set of training examples, each marked as belonging to one or the other of two or more categories, an SVM training algorithm builds a model that assigns new examples to one category or the other, making it a non-probabilistic binary linear classifier. A support vector machine constructs a hyperplane or set of hyperplanes in a high- or infinite-dimensional space, which can be used for classification, regression, or other tasks like outliers detection. Intuitively, a good separation is achieved by the hyperplane that has the largest distance to the nearest training-data point of any class (so-called functional margin), since in general the larger the margin the lower the generalization error of the classifier.

In computational complexity and communication complexity theories the decision tree model is the model of computation or communication in which an algorithm or communication process is considered to be basically a decision tree, i.e., a sequence of branching operations based on comparisons of some quantities, the comparisons being assigned the unit computational cost. Several variants of decision tree models have been introduced, depending on the complexity of the operations allowed in the computation of a single comparison and the way of branching. Decision trees models are instrumental in establishing lower bounds for computational complexity for certain classes of computational problems and algorithms: the lower bound for worst-case computational complexity is proportional to the largest depth among the decision trees for all possible inputs for a given computational problem. The computation complexity of a problem or an algorithm expressed in terms of the decision tree model is called decision tree complexity or query complexity.

According to a further embodiment, the method described herein is useful for monitoring a subject, specifically for measuring the response of a subject to stimulation of liver regeneration.

The method described herein can be used for monitoring therapies and treatment success of therapies such as chemotherapy, immunotherapy, portal vein embolization, associating liver partition and portal vein ligation for staged hepatectomy (ALPPS) or other therapy options such as exercise intervention ("prehabilitation"), diet or pharmacological therapy reducing portal vein hypertension.

Chemotherapy is treatment with drugs to destroy cancer cells. Examples of drugs effective as systemic chemotherapy in liver cancer are doxorubicin (Adriamycin), 5-fluorouracil, and cisplatin. But even these drugs shrink only a small portion of tumors, and the responses often do not last long. Even with combinations of drugs, in most studies systemic chemotherapy has not helped patients live longer. Alternatively, chemotherapy can be delivered directly to the liver in a process called hepatic artery infusion (HAI). HAI gets more chemotherapy to the tumor than systemic chemotherapy but doesn't increase side effects. Examples of chemotherapy administered via hepatic artery infusion include floxuridine (FUDR), cisplatin, mitomycin C, and doxorubicin.

Portal vein embolization (PVE) is a technique used before partial liver resection to increase the size of liver segments that will remain after surgery. This therapy redirects portal blood to segments of the future liver remnant (FLR), resulting in hypertrophy. PVE is indicated when the FLR is either too small to support essential function or marginal in size and associated with a complicated postoperative course. When appropriately applied, PVE has been shown to reduce postoperative morbidity and increase the number of patients eligible for curative intent resection. Preoperative portal vein embolization is a safe image-guided procedure that causes hypertrophy of the FLR by redirecting portal blood to the non-tumor-bearing liver.

Associating liver partition and portal vein ligation for staged hepatectomy (ALPPS) has been evolved recently as a salvage therapy for traditionally non-resectable liver tumors. The ALPPS procedure has first been described by Schnitzbauer et al. (27) and has been developed to allow for rapid liver regeneration, preferably in borderline operable patients that do not bear sufficient remnant liver to allow complete upfront resection of the diseased part of the liver. Specifically, it has opened a window to the patients with right hepatic lobe tumor with insufficient future liver remnant (FLR). The procedure is performed in two steps. Specifically, in a first step the portal vein branches, feeding the tumor bearing liver, are selectively ligated, while the arterial as well as bile structures are preserved and the liver parenchyma is further transsected during this initial step of surgery. If successful, this procedure leads to liver regeneration and liver growth within a few days. Specifically, once the liver has regenerated sufficiently a second surgical procedure is performed to remove the ligated remaining liver lobes. Major drawbacks of this procedure are high morbidity and mortality rates, and reliable predictive markers to determine when the risk of liver dysfunction is low enough to perform the second step of the resection are urgently needed.

Specifically, samples provided as described herein can be classified in "treatment success" or "no treatment success" employing the in vitro method using the miRNA signatures as described herein. Thereby, the success of liver regeneration following methods such as for example ALPPS, PVE or chemotherapy can be determined prior to partial liver resection. Specifically, time-points when risk of developing liver dysfunction following partial liver resection is low can be determined.

Portal hypertension is an increase in the blood pressure within a system of veins called the portal venous system. Veins coming from the stomach, intestine, spleen, and pancreas merge into the portal vein, which then branches into smaller vessels and travels through the liver. If the vessels in the liver are blocked due to liver damage, blood cannot flow properly through the liver. As a result, high pressure in the portal system develops. Treatment options reducing portal vein hypertension include endoscopic variceal ligation (EVL), the use of non-selective β-blockers (NSBB) such as propranolol or nadolol, which decrease portal pressure through a reduction in portal blood flow. Their mechanism of action involves decreasing cardiac output via β-1 receptors and causing splanchnic vasoconstriction by blocking β-2 receptors, resulting in unopposed α-1 activity. The latter is the most important effect and therefore it is essential that NSBB (as opposed to selective β-blockers) be used (Khurram and Guadalupe, *World J Gastroenterol.* 2012 Mar. 21; 18(11): 1166-1175).

In general, liver regeneration can also be stimulated by lifestyle changes such as increased exercise to improve overall fitness ("prehabilitation") and diet changes reducing protein, sodium and alcohol intake.

Further provided herein is a kit-of-parts comprising
a) detection reagents capable of detecting the expression level of at least one microRNA, selected from the group consisting of miR-151a, miR-192 and miR-122, in a subject's sample,
b) reference expression levels,
c) software comprising the classification models for comparison of expression levels of a) with expression levels of b) and for classification of the subject's sample into one of at least two classes, wherein each class is one of the at least two categories "high-risk" and "low-risk" of liver dysfunction after partial liver resection.

Specifically, the kit-of-parts provided herein can be a qRT-PCR kit comprising reagents for RNA extraction, cDNA synthesis and fluorescence-based amplification of specific microRNA target sequences, specifically at least miR-151a, miR-192 or miR-122. Fluorescent reporter probes detect only the DNA containing the sequence complementary to the probe; therefore, use of the reporter probe significantly increases specificity, and enables performing the technique even in the presence of other dsDNA. Using different-coloured labels, fluorescent probes can be used in multiplex assays for monitoring several target sequences in the same tube. These fluorescent reporter molecules include sequence specific probes as detection reagents such as Molecular Beacons, FRET Hybridization Probes, Scorpion Primers® or TaqMan® Probes. Various methods of detecting miRNA using qRT-PCR are known to the person skilled in the art, such as in Arya et al. (*Expert Rev Mol Diagn.* 2005 March; 5(2):209-19) and Navarro et al. (*Clin Chim Acta.* 2015 Jan. 15; 439:231-50).

Specifically, the kit-of-parts provided herein can be a microarray kit comprising a high-density or low-density array with capture probes for specific microRNA sequences, chemicals for microRNA labeling and hybridization and wash buffers to increase stringency and specificity of the hybridization reaction. microRNA labeling can be achieved using biotin probes such as for example Biotin-16-UTP from Lucigen.

Specifically, the kit-of-parts provided herein can be a next-generation sequencing kit comprising reagents required for 5' and 3' adapter ligation to microRNAs, reverse transcription and PCR amplification to obtain sequencing libraries suitable for next-generation sequencing.

The present invention further comprises the following items:

1. An in vitro method of determining a subject's risk of liver dysfunction, specifically after partial liver resection, said method comprising the steps of:
   a) providing a sample from said subject,
   b) determining in said sample the expression level of at least one miRNA, selected from the group consisting of miR-151a, miR-192 and miR-122, and
   i. comparing the expression level(s) of b) with at least one reference expression level, or
   ii. identifying the ratios of miR-151a to miR-192 and/or of miR-122 to miR-151a based on the expression levels determined in b), and comparing said expression level ratios with reference expression level ratios, and
   c) classifying the sample from the outcome of step i) or step ii) into one of at least two classes, wherein each class is one of the at least two categories "high-risk" and "low-risk".

2. The in vitro method of item 1, wherein the expression levels of miR-151a, miR-192 and miR-122 are determined.

3. The in vitro method of item 1 or 2, comprising further classes of the categories "no-risk" and "medium-risk".

4. The in vitro method of any one of items 1 to 3, wherein the reference expression level is the expression level of at least one miRNA, selected from the group consisting of miR-151a, miR-192 and miR-122 of a healthy subject or a subject without post-operative liver dysfunction or a group thereof.

5. The in vitro method of any one of items 1 to 3, wherein reference expression level ratios are expression level ratios of miR-151a to miR-192 and of miR-122 to miR-151a of a healthy subject or a subject without post-operative liver dysfunction or a group thereof.

6. The in vitro method of any one of items 1 to 5, wherein subjects classified as "low-risk" are subjected to partial liver resection, subjects classified as "medium-risk" are subjected to stimulation of liver regeneration before partial liver resection and subjects classified as "high-risk" are not subjected to partial liver resection.

7. The in vitro method of item 6, wherein subjects classified as "medium-risk" are subjected to treatment before partial liver resection, which treatment is selected from the group consisting of neoadjuvant chemotherapy, portal vein embolization, associating liver partition and portal vein ligation for staged hepatectomy (ALPPS), exercise intervention ("prehabilitation") or pharmacological therapy reducing portal vein hypertension.

8. The in vitro method of item 6, wherein subjects classified as "high-risk" are subjected to liver transplantation, palliative chemotherapy, radiofrequency ablation, or transarterial chemoembolisation (TACE).

9. An in vitro method of monitoring regeneration-success of liver regeneration stimulation of a subject, comprising the steps of
   a) providing a sample from said subject,
   b) determining the expression level ratios of miR-151a to miR-192 and of miR-122 to miR-151a in said sample
   c) determining the expression level ratios of miR-151a to miR-192 and of miR-122 to miR-151a in a reference sample, wherein the reference sample is an earlier sample of the subject,
   d) comparing the expression level ratios of b) with the expression level ratios of c), and
   e) classifying the sample of said subject from the outcome of the comparison of step d) into one of two categories, "regeneration-success" or "no regeneration-success".

10. The in vitro method of item 9, wherein the liver regeneration stimulation is selected from the group consisting of induction of liver hypertrophy by portal vein embolization, induction of liver hypertrophy by associating liver partition and portal vein ligation for staged hepatectomy (ALPPS), exercise intervention ("prehabilitation") to improve overall fitness, and pharmacological therapy reducing portal vein hypertension.

11. The in vitro method of any one of items 1 to 10, wherein the subject is suffering from malignant lesions in the liver, preferably metastatic colorectal cancer, hepatocellular carcinoma or cholangiocellular carcinoma, or from benign liver tumors, hepatic cysts and/or parasites.

12. The in vitro method of any one of items 1 to 11, wherein the sample is selected from the group consisting of blood, serum, plasma, specifically platelet-poor plasma, lymph, urine, saliva and biopsy probes.

13. The in vitro method of any one of items 1 to 12, wherein the expression levels or expression level ratios of the sample are compared with the reference expression level or expression level ratios using a classification model.

14. The in vitro method of any one of items 1 to 13, wherein a classification model classifies the sample of a subject from the outcome of the comparison with the reference into one of the at least two classes.

15. The in vitro method of any one of items 13 or 14, wherein the classification model is selected from the group consisting of logistic regression models, support vector machine models and decision tree models.

16. The in vitro method of any one of items 1 to 15, wherein the expression levels are determined using a method selected from the group consisting of a sequencing-based method, specifically next-generation sequencing, an array-based method and a PCR-based method, specifically a quantitative PCR-based method.

17. A kit-of-parts comprising
   a) detection reagents capable of detecting the expression level of at least one microRNA, selected from the group consisting of miR-151a, miR-192 and miR-122, in a subject's sample,
   b) reference expression levels,
   c) software comprising the classification models for comparison of expression levels of a) with expression levels of b) and for classification of the subject's sample into one of at least two classes, wherein each class is one of the at least two categories "high-risk" and "low-risk" of liver dysfunction, specifically after partial liver resection.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Using next-generation sequencing as an unbiased systematic approach 554 miRNAs were detected in preoperative plasma of 21 patients suffering from postoperative LD after liver resection and 27 matched controls. Subsequently, an miRNA signature—comprising miRNAs 151a-5p, 192-5p and 122-5p—was detected that highly correlated with patients developing postoperative LD after liver resection. The predictive potential for postoperative LD was subsequently confirmed using real-time PCR in an independent validation cohort of 24 patients. Ultimately, a regression model of the two miRNA ratios 151a-5p to 192-5p and 122-5p to 151a-5p reliably predicted postoperative LD, severe morbidity, prolonged intensive care unit stay as well as hospitalization and even mortality prior to surgery with a remarkable accuracy, thereby outperforming established markers of postoperative LD.

Given the clinical relevance of predicting potentially fatal postoperative clinical outcome after liver resection, this data demonstrates the clinical utility of a novel miRNA-based biomarker to support the selection of patients undergoing partial hepatectomy. These biomarkers allow tailoring of treatment and surgical strategies to the specific risk profile of individual patients.

Materials and Methods

Study Population

Initially a discovery cohort of patients undergoing liver resection at the Medical University of Vienna was prospectively recruited starting from February 2012. Patients with either hepatocellular carcinoma (HCC), cholangiocellular carcinoma (CCC) or metastatic colorectal carcinoma (mCRC), were considered eligible for inclusion. Subsequently, as we observed a significant predictive potential of miRNAs for postoperative LD and clinical outcome, we validated our explorative results in a prospective set of patients undergoing liver resection.

Baseline characteristics, extent of surgical resection (<3 segments=minor, segments=major, according to the IHPBA Brisbane 2000 nomenclature (13)) and intraoperative individualities, as well as preoperative variables of liver function and damage were prospectively recorded in all patients.

The present study was approved by the Institutional Ethics Committee and in accordance with the Declaration of Helsinki and written informed consent was given by all patients. In addition, the trial was registered at a clinical trials registry (ClinicalTrials.gov Identifier: NCT01700231 and NCT02113059).

Definition and Classification of Postoperative Complications

Patients were followed up for a postoperative period of 90 days at the Medical University of Vienna. Postoperative outcome was prospectively documented. Postoperative LD was diagnosed following the criteria issued by the International Study Group of Liver Surgery (ISGLS) (14). Briefly, LD was defined by both abnormal values of serum bilirubin and prothrombin time on or after postoperative day (POD) 5. Of note, in case of abnormal preoperative serum bilirubin or prothrombin time, a postoperative deviation and deterioration on two subsequent days after POD 5 was identified as postoperative LD. Furthermore, patients reaching normal serum bilirubin or prothrombin time values prior to POD 5, or were discharged early due to good clinical performance and hence, had no further blood collection, were considered as "no LD".

For classification of patients with postoperative morbidity the outline given by Dindo et al. (15) was applied. Accordingly, the degree of postoperative complications was recorded and graded from I to V. In case of multiple complications, the most serious one was used for classification. In addition, the length of postoperative hospitalization and stay at the intensive care unit (ICU) was recorded. Ultimately, death within 90 days after surgery was classified as postoperative mortality (16).

Assessment of Preoperative Liver Function

Liver Function was routinely assessed prior to liver resection using the indocyanine green (ICG)-clearance (17). 25 mg of ICG reagent were solved in 20 ml of isotonic fluid and a dose of 0.25 mg/kg of body weight was intravenously administered to the patient. Concentration of the color reagent in the circulation was assessed using pulse spectrometry. Ultimately, the amount of ICG reagent cleared within the first minute (=plasma disappearance rate (PDR)), as well as the remaining amount of reagent detected in the circulation after 15 minutes (R15), were measured in the present patient cohort.

Measurement of Circulating miRNAs

Prior to the operation meticulous preparation of plasma was performed as previously described (18, 19). Briefly, blood was drawn into pre-cooled CTAD tubes and processed within 30 minutes. Plasma was separated from solid blood components via centrifugation at 1000 g and 4° C. for 10 minutes, followed by an additional centrifugation step for 10 minutes at 10 000 g and 4° C. Ultimately, plasma was stored at −80° C. until further analysis.

RNA Extraction

The miRNeasy Mini Kit (Qiagen, Germany) was applied to isolate total RNA, including small RNAs, from plasma. Frozen plasma samples were thawed at room temperature and centrifuged at 12 000 g for 5 minutes to separate potential debris from cell-free component. 200 μl of plasma were mixed by vortexing with 1 ml Qiazol containing a mix of three synthetic spike-in controls (Exiqon, Denmark). Following incubation at room temperature for 10 minutes, 200 μl chloroform were added and vigorously mixed by vortexing. After centrifugation at 12 000 g for 15 minutes at 4° C., 650 μl of aqueous phase were aspirated. Glycogen (Ambion, USA) was added to a final concentration of 50 μg/ml. Samples were then transferred to silica columns and further processed using the QIAcube liquid handling robot according to the manufacturer's protocol. RNA was precipitated with 750 μl Ethanol, triple washed with RPE-buffer, followed by RNA-elution in 30 μl nuclease free water and stored at −80° C.

Small RNA Sequencing

Small RNA sequencing libraries were generated using the CleanTag SmallRNA library preparation kit (TriLink, USA) according to the manufacturer's recommendations. Two μl total RNA were used for sequential 3' and 5' adapter ligation at 28° C. for 1 hour, followed by 65° C. for 20 minutes. Adapters were prediluted 1:12 to account for low RNA abundance. Reverse transcription was performed at 50° C. for 1 hour. PCR amplification was performed using barcoded Illumina primers for small RNA sequencing: 26 cycles of denaturation (98° C., 10 s), annealing (60° C., 30 s) and elongation (72° C., 15 s) were used. PCR products were purified using the QiaQuick protocol (Qiagen, Germany), and size checked by capillary electrophoresis using the DNA 1000 Chip (Agilent, USA). The ~145 bp peak concentration was used as a basis for pooling equimolar amounts of DNA. The pool was gel purified to select for template inserts between 18 and 50 bp. Sequencing was performed on an Illumina NextSeq 500, single-end reads with 50 cycles (Illumina, USA). Sequencing reads in fastq format were adapter-trimmed and quality checked (generation of fastQC files). Quality filtered reads (phred>30) were used for alignment against human mature miRNAs (miRBase v21) using Bowtie2. Mapped reads were cross-check through genome aligments (Bowtie2, GRCh37). Mature miRNA reads were counted (isomiR sequences were summarized) and normalized as counts per million (CPM) to the total number of mapped reads. CPM values were used for statistical analysis (see below).

qPCR Analysis qPCR analyses were performed as previously described (20). Briefly, 2 µl of total RNA were reverse transcribed into cDNA using the Universal cDNA Synthesis Kit II (Exiqon, Denmark). cDNA was pre-diluted 1:50 for qPCR amplification using the Exilent SYBR® Green masermix and LNA-modified primer-pairs (Exiqon, Denmark). qPCR amplifications were run on an LC480-II (Roche Diagnostics, Germany) in 96- or 384-well format. Cq-values were determined using the second-derivative method. Robustness of RNA extraction, cDNA synthesis and qPCR amplification was assessed using combinations of synthetic spike-in controls (Exiqon, Denmark). Hemolysis was assessed using the ratios of miR-23a-3p and miR-451a (21). Of note, no samples failed due to hemolysis or high analytical variance.

Statistical Analyses

Differences in patients' characteristics between the discovery cohort and the validation cohort for categorical variables were tested by chi-squared test and for continuous variables by Wilcoxon's rank-sum test.

Normalization and calculation of differentially expressed microRNAs between patient groups with LD versus without LD (log 2 fold changes) were performed using the R package edgeR. Significant differences were identified by likelihood ratio tests. P-values were adjusted for multiple testing based on the false discovery rate according to the Benjamini-Hochberg method. MicroRNAs with an average abundance of log 2 counts per million (logCPM)>5, fold change>1.3, and raw p<0.2 were considered as potential biomarker candidates. For qPCR analyses microRNAs were pairwise self-normalized: for a pair of microRNAs (miR1, miR2) the $\log_2$ ratios of expression values log 2(miR1/miR2) were calculated by difference in their Cq values ($\Delta Cq = Cq_{miR2} - Cq_{miR1}$). To compare results for microRNA pairs from NGS analyses (log 2 fold change) with results from qPCR analyses ($\Delta Cq$) linear regression analyses were performed. The linear association was tested by a two-sided Wald test for the respective coefficient and the coefficient of determination ($R^2$) was calculated. Distribution and differences of $\Delta Cq$ values between the control and LD group were shown by boxplots and tested using a two-sided Wilcoxon rank-sum test.

Random forest analyses were performed (R package randomForest with standard settings and grewing 10,001 trees) to identify most important variables (microRNA pairs) in classification of patients with LD versus without LD. For classification, each of the 2 most informative microRNA pairs were included in a univariate and multivariate logistic regression model. A leave-one-out cross validation (LOOCV) strategy was applied and evaluated by a receiver operating characteristics (ROC) analysis (R package ROCR). The area under the ROC curve (AUC) was determined and significant deviation from a random assignment (AUC=0.5) was tested. The performance of these logistic regression classification models was evaluated in an independent validation cohort using ROC analyses. To identify optimal (clinically relevant) classification cutoffs, for different cutoffs contingency tables (TP,FP;FN,TN) and associated parameters (including sensitivity (SN), specificity (SP), positive prediction value (PPV), negative prediction value (NPV, accuracy (ACC), F1-score (F1), Matthews correlation coefficient(MCC)) were calculated based on the multivariate logistic regression model including the 2 microRNA pairs learned in the discovery cohort. Two cutoffs were selected 1) by maximal MCC and 2) PPV=1 (false positives FP=0) and maximal MCC. Applying the selected model and these criteria resulted in the same cutoffs for the discovery set, the validation set, and the combined set. For comparison of the classification performance with other clinical parameters the combined set was used. Using ROC analyses and AUC the performance of this 2 microRNA pair model was compared to other liver function parameter. For the two respective cutoffs the difference in the portion of patients with liver dysfunction, with severe morbidity, and mortality between predicted controls and predicted liver dysfunction were tested by two-sided Fisher exact test and odds ratios (OR) were determined.

Analyses were performed using SPSS (version 23.0) and R (version 3.4.1); p-values<0.05 were considered significant.

Example 1: Establishing the Predictive miRNA Panel for Liver Dysfunction Post-Surgery in the Discovery Cohort A total of 48 patients with either mCRC, HCC or CCC who underwent liver resection between February 2012 and April 2016 were included in our discovery cohort. To achieve a representative cohort, 21 patients suffering from postoperative LD were matched based on basic characteristics, liver function and extend of liver resection to 27 patients without postoperative LD. Subsequently, additional 24 patients served as a prospective, clinically relevant validation cohort. Patient characteristics are shown in Table 2 and were compared between the discovery and the validation cohort. Of note, given the selection of the discovery cohort, there was a significantly higher number of patients undergoing major liver resection in the discovery cohort, which was paralleled by significantly worse ICG-clearance and gamma-glutamyl transpeptidase values.

TABLE 2

| Parameter | Entire Cohort (N = 72) Median (range) N (%) | Evaluation Cohort (N = 48) Median (range) N (%) | Validation Cohort (N = 24) Median (range) N (%) | p-value |
|---|---|---|---|---|
| Patient Demographics | | | | |
| Gender | | | | 0.721 |
| Male | 50 (69.4%) | 32 (66.7%) | 18 (75.0%) | |
| Female | 22 (30.6%) | 16 (33.3%) | 6 (25.0%) | |
| Age(years) | 66 (35-89) | 65 (36-89) | 66 (35-86) | 0.693 |
| Hepatic Resection | | | | <0.001 |
| Minor (<3 segments) | 16 (22.2%) | 4 (8.3%) | 12 (50.0%) | |

TABLE 2-continued

Patient Demographics

| Parameter | Entire Cohort (N = 72) Median (range) N (%) | Evaluation Cohort (N = 48) Median (range) N (%) | Validation Cohort (N = 24) Median (range) N (%) | p-value |
|---|---|---|---|---|
| Major (≥3 segments) | 56 (77.8%) | 44 (91.7%) | 12 (50.0%) | |
| Tumor Type | | | | 0.117 |
| CRCLM | 27 (37.5%) | 16 (33.3%) | 11 (45.8%) | |
| HCC | 22 (30.6%) | 16 (33.3%) | 6 (25.0%) | |
| CCC | 21 (29.2%) | 16 (33.3%) | 5 (20.8%) | |
| Other | 2 (2.8%) | 0 (0.0%) | 2 (8.3%) | |
| Cofactors | | | | |
| Neoadjuvant CTx | 24 (33.3%) | 16 (33.3%) | 8 (33.3%) | 0.904 |
| Steatosis (%) | 8 (0-100) | 5 (0-40) | 10 (0-100) | 0.209 |
| Steatohepatitis | 16 (22.2%) | 10 (20.8%) | 6 (25.0%) | 0.447 |
| Fibrosis | 33 (45.8%) | 19 (39.5%) | 14 (58.3%) | 0.418 |
| Cirrhosis | 7 (9.7%) | 4 (8.3%) | 3 (12.5%) | 0.847 |
| Intraoperative RBC | 9 (11.1%) | 7 (14.6%) | 1 (4.2%) | 0.399 |
| Preoperative Parameters | | | | |
| PDR(%) | 22.1 (9.9-39.4) | 20.0 (9.9-34.8) | 24.0 (16.2-39.4) | 0.017 |
| R15(%) | 4.0 (0.3-22.7) | 5.0 (0.5-22.7) | 2.6 (0.3-17.0) | 0.056 |
| Platelets(×10$^3$/μl) | 234 (86-492) | 236 (86-492) | 228 (113-470) | 0.872 |
| SB(mg/dl) | 0.58 (0.15-3.17) | 0.57 (0.15-3.17) | 0.64 (0.27-1.54) | 0.256 |
| PT(%) | 101 (40-137) | 102 (40-137) | 100 (61-132) | 0.201 |
| AP(U/l) | 99 (45-707) | 104 (49-707) | 79 (45-418) | 0.053 |
| GGT(U/l) | 69 (16-1576) | 32 (17-224) | 48 (16-699) | 0.043 |
| AST(U/l) | 30 (14-224) | 33 (9-318) | 27 (14-67) | 0.065 |
| ALT(U/l) | 32 (9-318) | 84 (18-1576) | 27 (13-66) | 0.164 |
| Albumin(g/l) | 42.5 (31.5-48.5) | 42.6 (31.5-47.3) | 42.3 (34.0-48.5) | 0.848 |
| Morbidity | | | | 0.838 |
| No Morbidity | 32 (44.4%) | 21 (43.8%) | 11 (45.8%) | |
| Grade I | 7 (9.7%) | 4 (8.3%) | 3 (12.5%) | |
| Grade II | 11 (15.3%) | 7 (14.6%) | 4 (16.7%) | |
| Grade III | 13 (18.1%) | 9 (18.8%) | 4 (16.7%) | |
| Grade IV | 4 (5.6%) | 2 (4.1%) | 2 (8.3%) | |
| Grade V | 5 (6.9%) | 5 (10.4%) | 0 (0.0%) | |
| Liver Dysfunction ISGLS | | | | 0.102 |
| No Liver Dysfunction | 46 (63.9%) | 27 (56.3%) | 19 (79.2%) | |
| ISGLS A | 6 (8.3%) | 5 (10.4%) | 1 (4.2%) | |
| ISGLS B | 7 (9.7%) | 4 (8.3%) | 3 (12.5%) | |
| ISGLS C | 13 (18.1%) | 12 (25.0%) | 1 (4.2%) | |
| Postoperative Stay | | | | |
| ICU (days) | 1 (0-15) | 1 (0-15) | 1 (0-12) | 0.103 |
| Total Hospitalization (days) | 10 (3-61) | 11 (4-50) | 9 (3-61) | 0.298 |

CRCLM = colorectal cancer liver metastases, HCC = hepatocellular carcinoma, CCC = cholangiocellular carcinoma, CTx = chemotherapy, RBC = red blood cells, PDR = plasma disappearance rate, R15 = retention rate at 15 minutes, SB = serum bilirubin, PT = prothrombin time, AP = alkaline phosphatase, GGT = gamma-glutamyl transpeptidase, AST = aspartate aminotransferase, ALT = alanine aminotransferase, ISGLS = international study group on liver surgery, ICU = intensive care unit.

For initial identification of miRNAs associated with post-operative liver dysfunction, it was aimed for an unbiased systematic approach using next-generation sequencing. Accordingly, miRNA profiles in plasma of all patients within the discovery cohort prior to surgery were analyzed to determine if miRNA profiles differ between patients that develop LD and those without delayed hepatic recovery. A total of 554 miRNAs across all analyzed plasma samples were detected. To identify potential biomarker candidates, cutoffs for plasma abundance (average log 2 count per million (logCPM)>5), effect size (fold change>1.3) and significance level (p<0.2) were implied. As depicted in FIG. 1, a set of 19 miRNAs remained in the analysis, of which 12 were up-regulated (right side) and 7 down-regulated (left side) in pre-operative plasma of patients with LD.

Figure 2A:
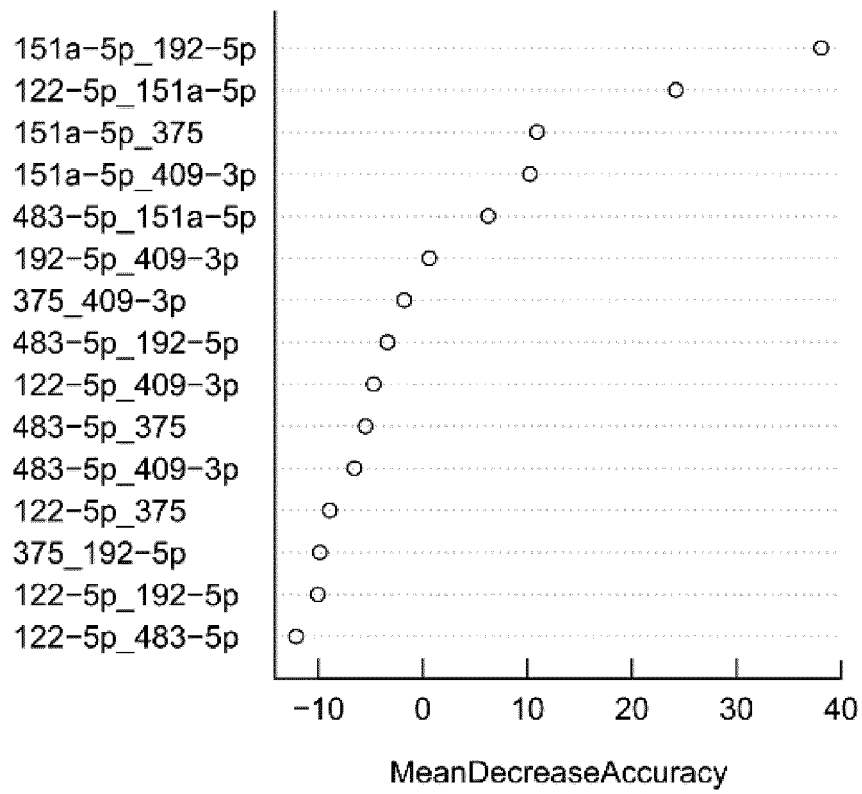
Figure 2B:
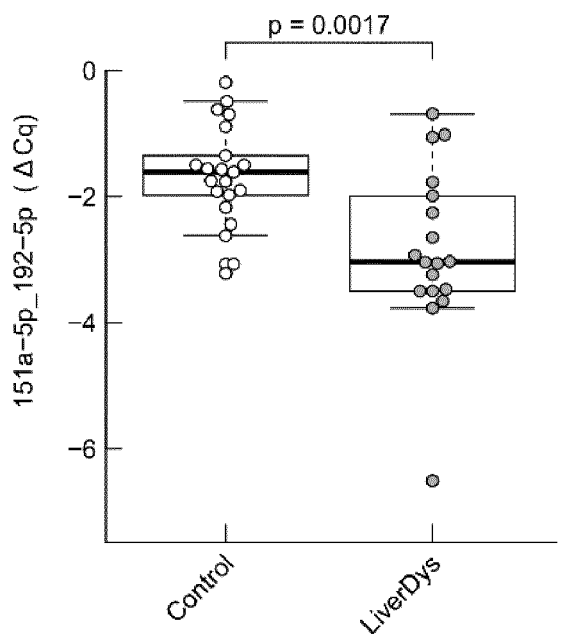
Figure 2C:
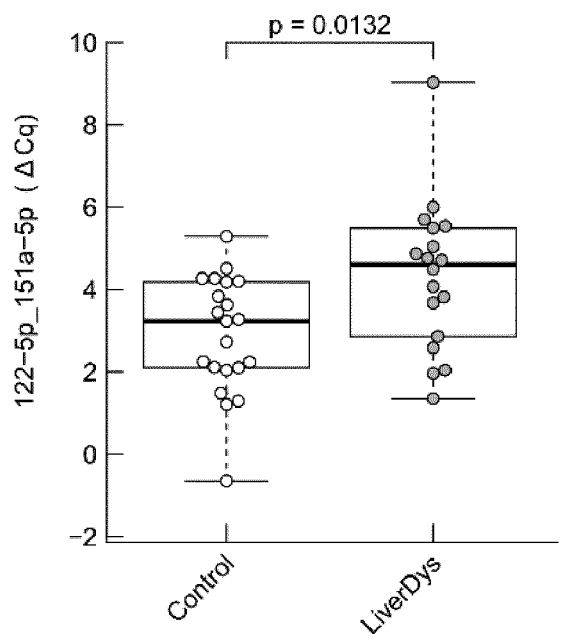
Figure 2D:
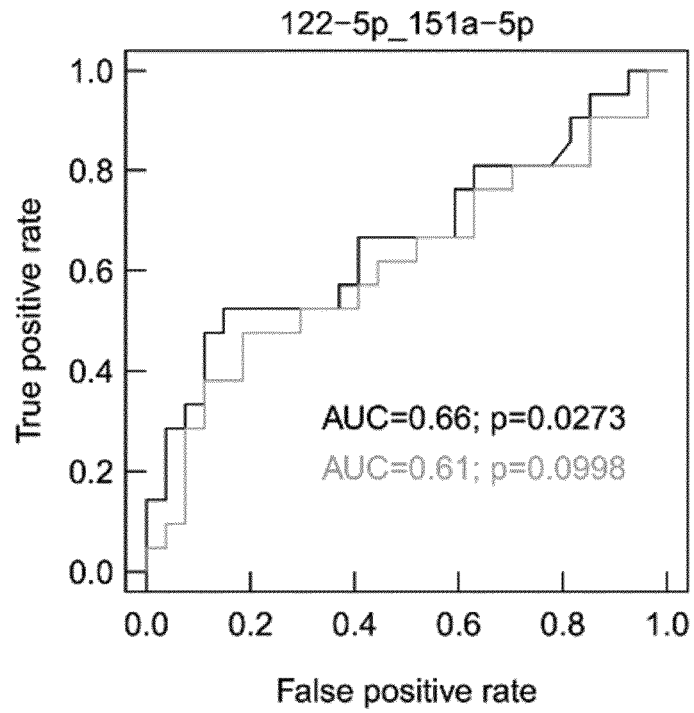
Figure 2E:
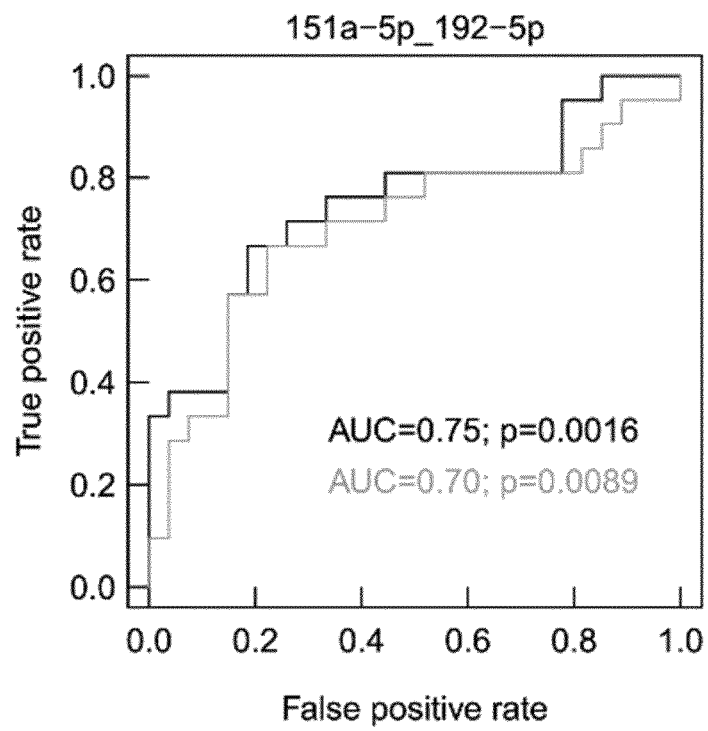
Figure 2F:
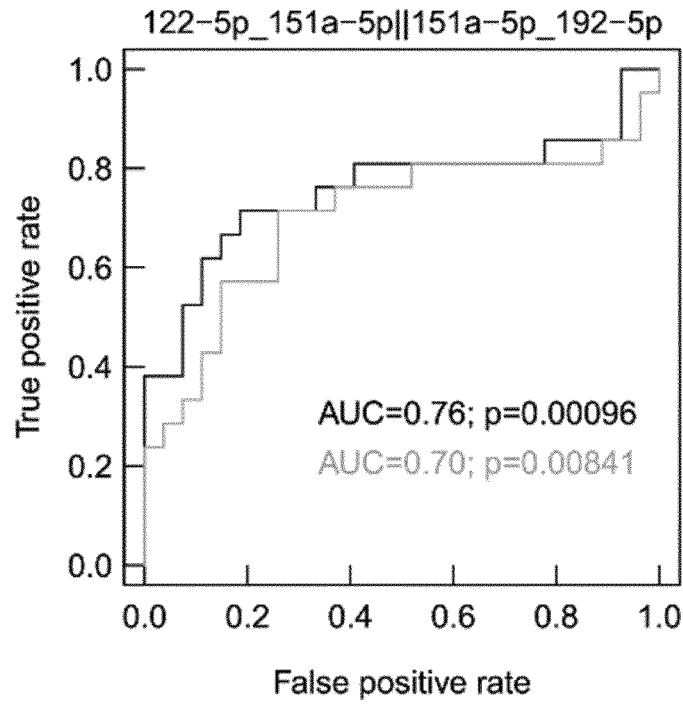
Figure 2G:
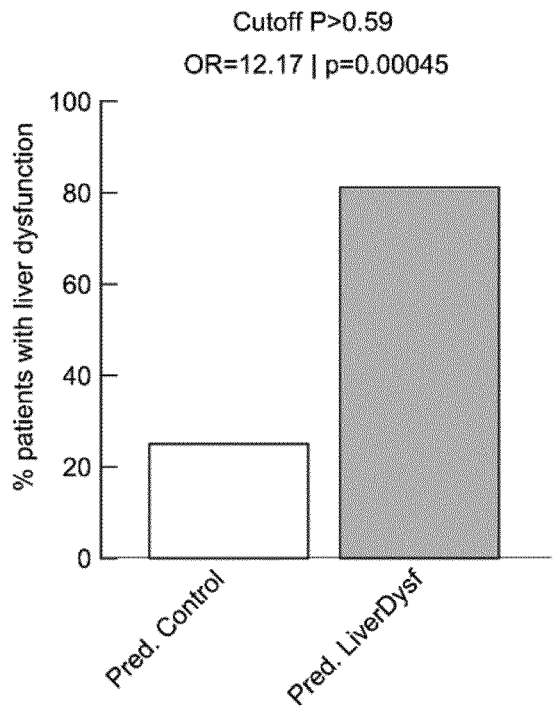
Figure 2H:
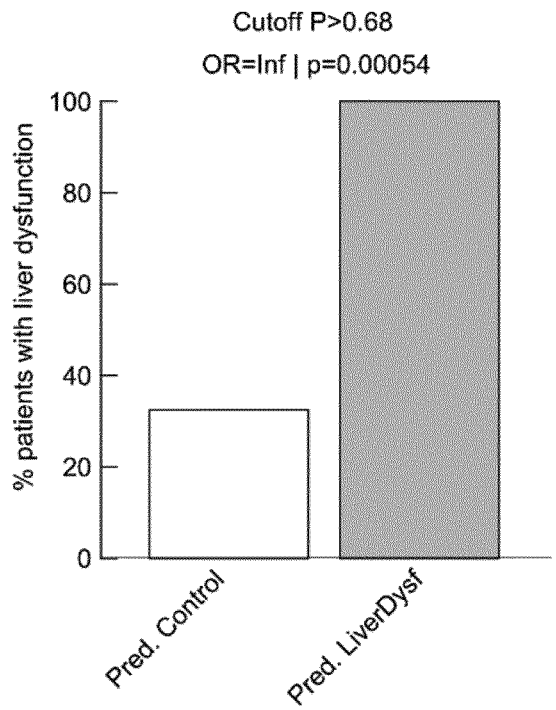

Subsequently, the analytical variability between next-generation sequencing and qPCR-based miRNA detection was analyzed and the relative logarithmic differences between two miRNAs to form self-normalizing miRNA pairs calculated, thus circumventing the need for a reference miRNA. Six of the top miRNAs, and consequently 15 miRNA pairs were considered for this analysis. High concordance between datasets (next-generation sequencing vs. qPCR-based miRNAs) was observed. The importance of miRNA pairs for achieving excellent predictive performance of negative post-operative outcomes was analyzed using random forest modelling (FIG. 2A). Two top-ranked miRNA pairs were identified (151a-5p/192-5p, 122-5p/151a-5p) with significant pre-operative differences between individuals developing LD and controls (FIG. 2B, C). The performance is described by the area under the curve (AUC) and whether the classification deviate significantly from the random assignment (AUC=0.5) is indicated by the p-value. The diagnostic performance of a multivariate model as measured by ROC analysis estimated an AUC of 0.66 for miRNA pair 122-5p_151a-5p (FIG. 2D), 0.75 for miRNA pair 151a-5p_192-5p (FIG. 2E) and 0.76 for a logistic regression model using the combination of both miRNA pairs (FIG. 2F).

Next, two clinically useful cut-offs were defined to predict postoperative LD. Accordingly, a low stringency cut-off was defined to identify patients that can undergo liver resection with very low risk (cut-off P>0.59) as well as a stringent cut-off, to identify patients that should be optimized prior to surgery or not undergo liver resection (cut-off P>0.68) were defined. The percentage of true postoperative LD on predicted controls and predicted LD were analysed for both model defined cut-offs P>0.59 and P>0.68. Both were found to be associated with a significant increase in postoperative LD (p=0.00045, FIG. 2G and p=0.00054, FIG. 2H). Specifically, 100% of patients with a Probability Score of higher than 0.68 developed liver dysfunction after partial liver resection. Whereas only 80% of the patients with a Probability Score of higher than 0.59 developed liver dysfunction and about 80% of subjects with a Probability Score lower than 0.59 did not develop liver dysfunction. These results show that a Probability Score P>0.68 is a good cutoff to classify patients as "high-risk" of developing liver dysfunction and a Probability Score of P>0.59 is a good cutoff to classify patients as "medium-risk" of developing liver dysfunction.

Figure 3A:
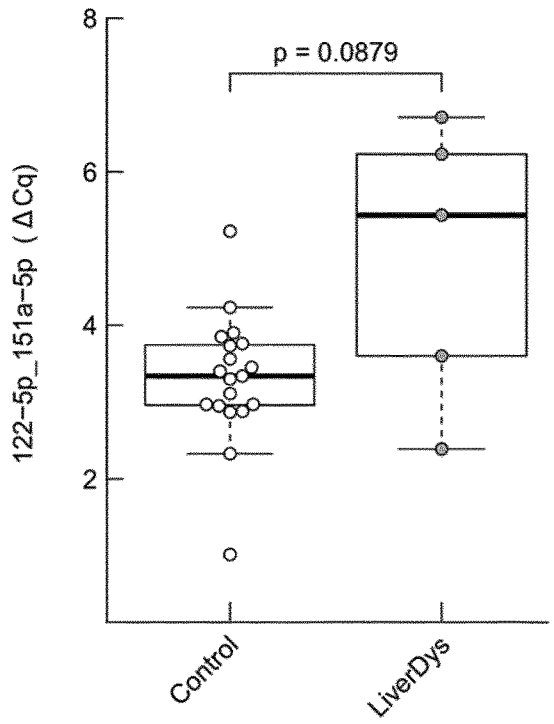
Figure 3B:
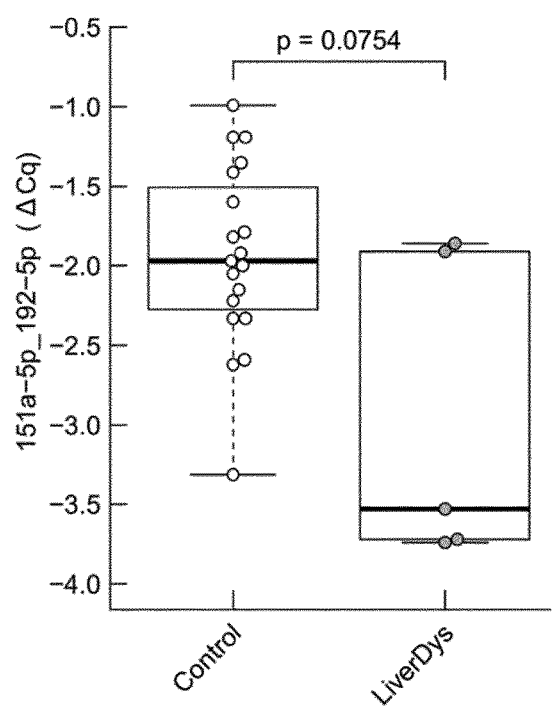
Figure 3C:
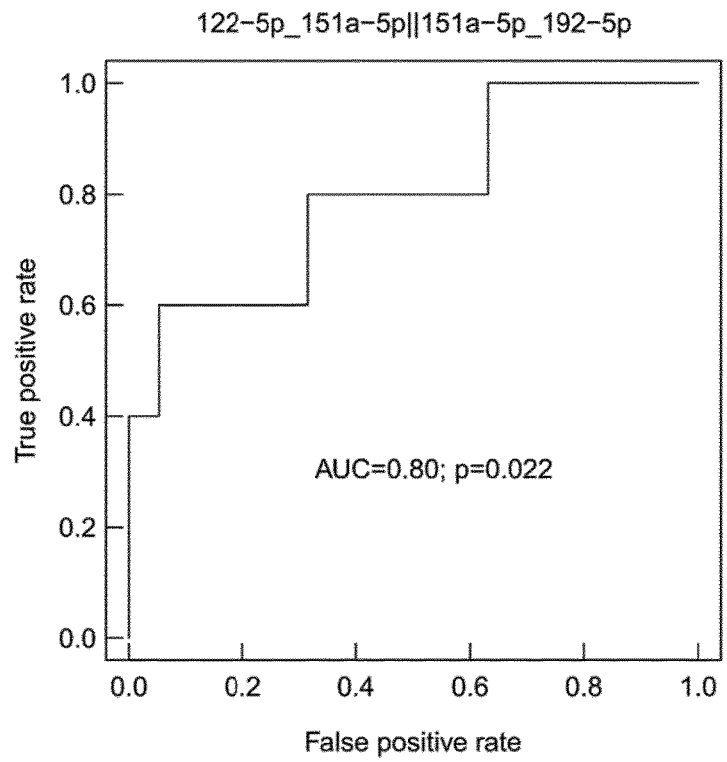

Example 2: Validation of the Discovered miRNA Ratios in an Independent Validation Cohort To confirm the clinical utility of the identified miRNA ratios, the predictive performance of the 2 miRNA pairs was validated in an independent prospective validation cohort consisting of 24 patients, 19 without and 5 with postoperative LD, reflecting the natural incidence of 30% post-surgical LD. As depicted in FIG. 3A for the miRNA pair 122-5p/151a-5p and FIG. 3B for the miRNA pair 151a-5p/192-5p there was a strong trend towards differentially regulated miRNAs in patients with LD compared to controls already within this small sample size. The diagnostic performance of a multivariate model as measured by ROC analysis showed an excellent AUC of 0.80 for the 2 miRNA pairs (FIG. 3C). Further, it was validated that the two cut-offs were able to predict postoperative LD for cut-off P>0.59 with p=0.018 (FIG. 3D) and for cut-off P>0.68 with p=0.036 (FIG. 3E), respectively.

Figure 4A:
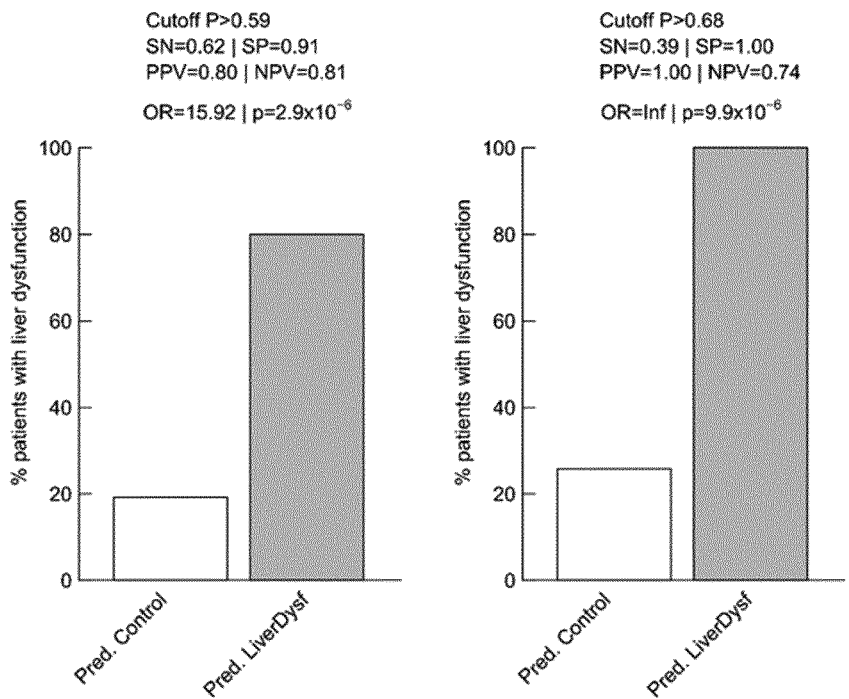
Figure 4B:
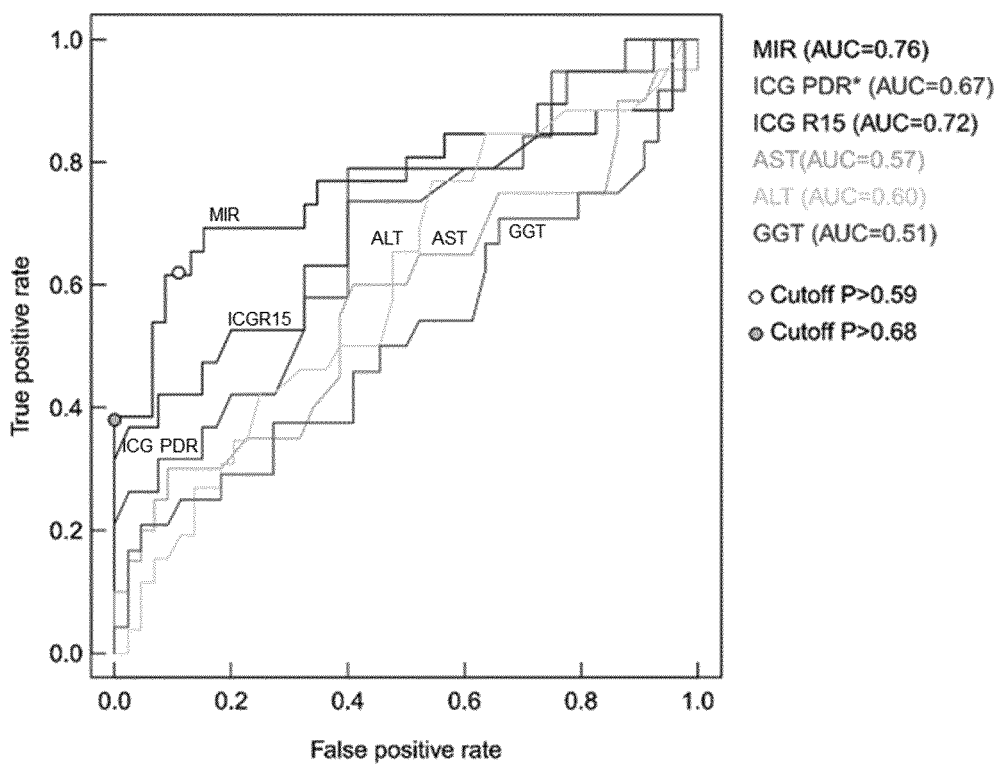
Figure 4C:
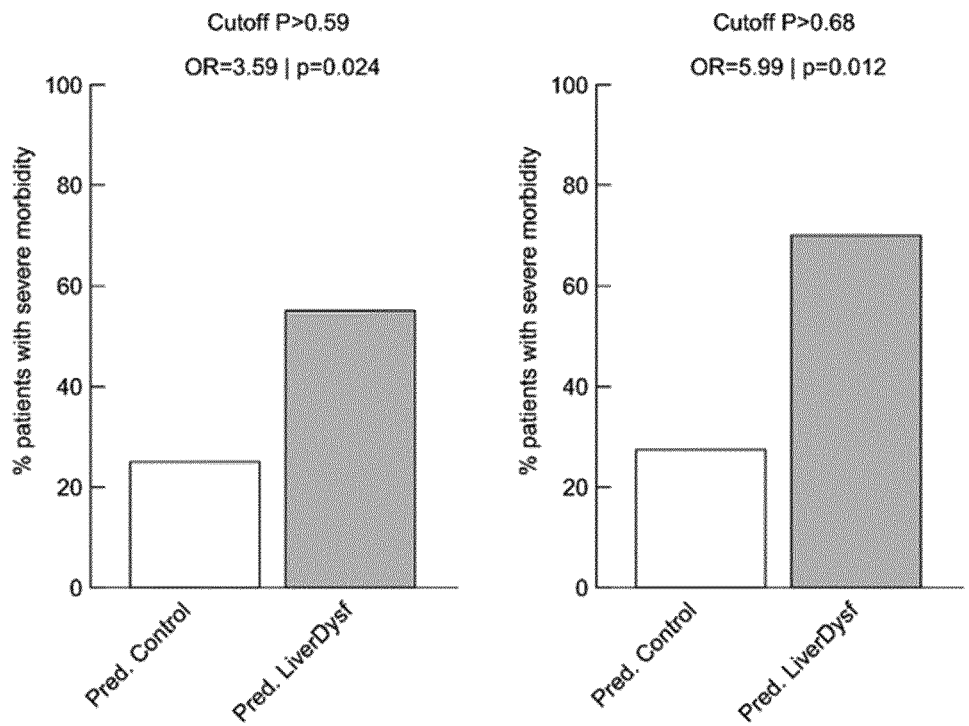
Figure 4D:
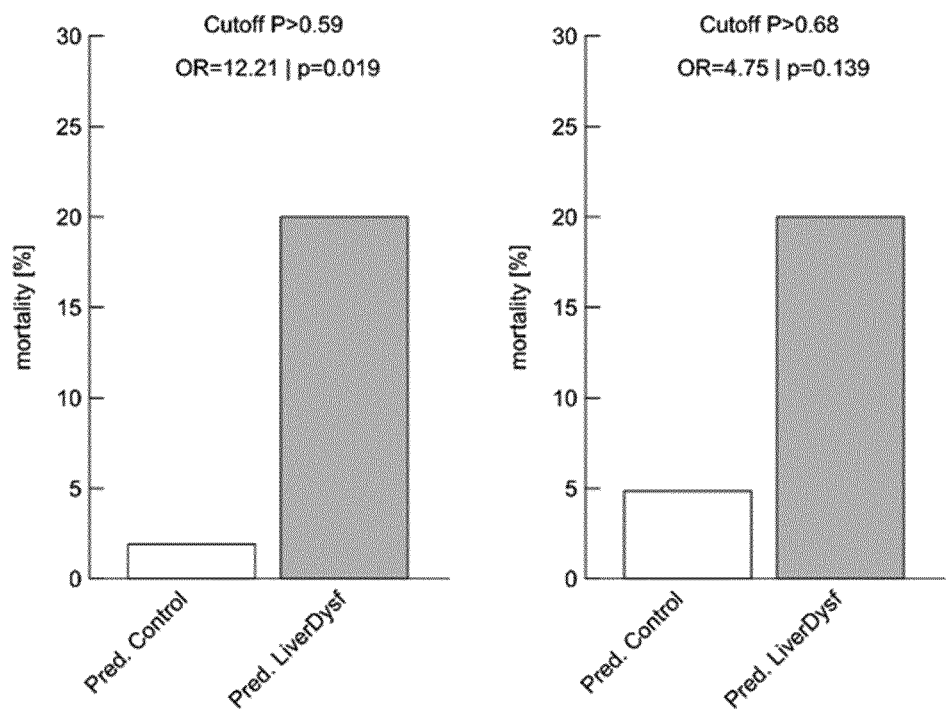
Figure 4E:
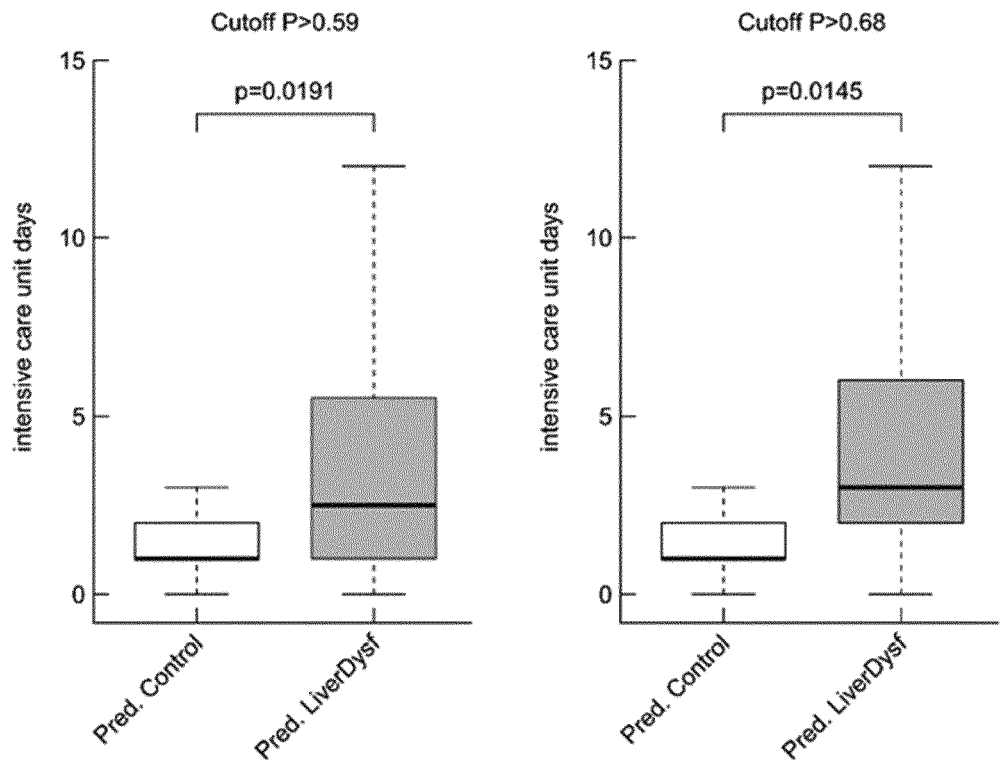
Figure 4F:
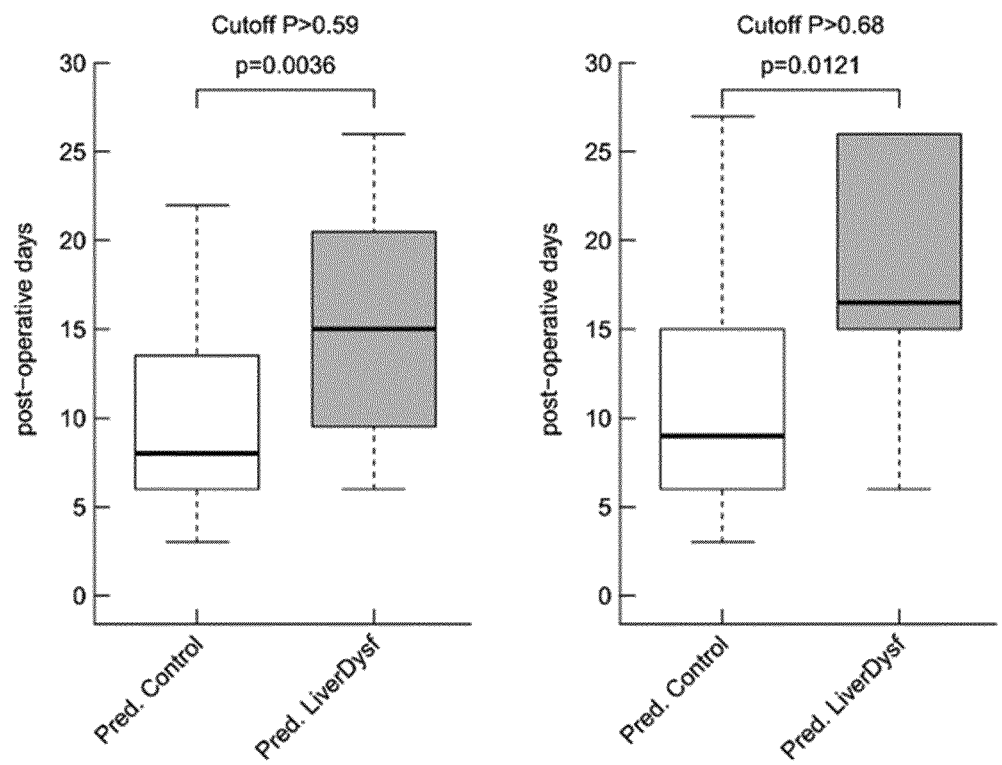

Example 3: Comparison of the Discovered miRNA Ratios to Other Predictors for Postoperative LD Next, the performance of the miRNA based prediction model was evaluated in the combined dataset (N=72). Therefore, the diagnostic performance of the two cut-offs were illustrated using sensitivity (SN), specificity (SP), positive predictive value (PPV), negative predictive value (NPV) and the odd's ratio (OR). The low stringency cut-off (>0.59) yielded balanced PPV and NPV values (0.80 and 0.81, respectively, while the stringent cut-off (>0.68) resulted in a PPV of 1.0, with an acceptable NPV of 0.74 (FIG. 4A), indicating that all patients tested positive suffered from post-operative LD, while 74% of patients tested negative did not suffer from post-operative LD. Vice-versa, 26% of patients tested negative did in fact suffer from post-operative LD. The ORs for an adverse event were 15.92 (p<0.0001) and infinite (p<0.0001), respectively. Receiver operator characteristics (ROC) curve analysis was performed for the microRNA model to compare its performance against that of standard liver function parameters. ROC curve analysis was performed for the miRNA model and compared with ROC curves of standard liver function parameters (FIG. 4B). An AUC of 0.76 for the miRNA model was observed, which exceeded the AUC of other parameters, including ICG plasma disappearance and retention rate as well as standard blood parameter like alanine transaminase (ALT), aspartate transaminase (AST) and gamma-glutamyltransferase (GGT). Finally, ORs for other adverse post-operative outcomes were analysed for both cut-off models. ORs for severe morbidity reached significance for both cut-offs (FIG. 4C). While OR for mortality was found to be significant for the low-stringency cut-off, the high-stringency cut-off, while showing the same trend, was not significant (FIG. 4D). Further, patients fulfilling our cut-offs were found to stay significantly longer on the ICU and remained hospitalized for a prolonged time (FIG. 4E, F).

Using next-generation sequencing, as an unbiased systematic approach, 554 miRNAs were detected in plasma of patients prior to liver resection. Of those, a signature was identified—consisting of 3 miRNAs 151a-5p, 192-5p and 122-5p—that specifically detected patients prior to surgery that developed postoperative LD after liver resection. In particular, a regression model of the two miRNA ratios 151a-5p to 192-5p and 122-5p to 151a-5p was found to reliably predict postoperative LD, severe morbidity, prolonged ICU as well as hospital stay and even mortality prior to surgery with a remarkable accuracy and without the need for a reference miRNA. Given the clinical relevance of predicting potentially fatal postoperative clinical outcome after liver resection, the data presented herein demonstrate the clinical utility of miRNA-based biomarkers to support the selection of patients undergoing partial hepatectomy the first time.

Specifically, in early stages of liver disease, clinical evaluation and quantification of liver function remains challenging. However, even slightly diminished liver function can become of major relevance if certain stressors, such as extensive liver resection, come into play. While several invasive and non-invasive tests have been developed, only few have found their way into routine clinical application. Major drawbacks of available predictors are availability, high costs and invasiveness (22). While hepatic venous pressure gradient (HVPG) has been shown to be of value to predict postoperative clinical outcome in HCC patients (23-25), it remains reserved for high-risk patients due to its invasiveness. Other less invasive and well-established markers to assess liver function rely on dynamic functional assessment of the liver. In this context, multiple groups have documented that ICG-clearance is vital to predict postoperative LD and morbidity (26). The data presented herein shows that the miRNA signatures described herein outperform ICG in terms of diagnostic accuracy by far. Importantly, ICG-clearance testing and most other liver function assessments are fairly expensive and time consuming, when compared to assessment of miRNA signatures. In addition, the advantage of plasma as a tool for precision medicine in these patients allows for a simple minimal invasive and easily accessible method.

Taken together, miRNA signatures were identified, which predict clinical outcome after liver resection with a remarkable accuracy, thereby outperforming established markers of postoperative LD.

These novel markers provide an improved strategy to identify patients that will not benefit from surgery or may even suffer from potentially lethal complications. Thereby, they allow tailoring surgical strategies to the specific risk profile of individual patients in an easy, cost effective and non-invasive manner. This could path the way to personalize liver surgery in patients with liver tumours and thereby increase therapeutic effectiveness, quality of patient's life and dramatically reduce health care costs.

Example 4: Dynamic Monitoring of Liver Function Recovery after Liver Resection to Guide Selection of Time Points for Surgery After validation of the predictive potential of miRNA ratios for postoperative outcome after liver resection, dynamical changes of miRNA pairs after surgery were determined to evaluate their association with liver function. Accordingly, a matched cohort of 3 patient groups was included in the study: 1: patients with regular liver resection without postoperative liver dysfunction (N=7); 2: patients with regular liver resection with postoperative liver dysfunction (N=8); 3: patients undergoing the ALPPS procedure with an augmented postoperative liver regeneration (N=8, see details on the procedure in FIG. 5A and in the description below). Details of the patient groups are provided in Table 3 below.

miRNA pairs were assessed as described in Example 1, and miRNA signatures were determined preoperatively as well as on the 1st and 5th postoperative day, POD1 and POD5, respectively. It was observed that in all patients, miRNA pairs as well as the combined liver dysfunction probability (p) changed significantly after liver resection to a comparable level (FIG. 5B), and that most of them recovered till postoperative day 5 in parallel with a regular liver function recovery.

In addition to the dynamic changes of miRNA pairs, it was to be determined whether their absolute value after surgery could be used to determine the optimal time point for the second step of the ALPPS procedure. The ALPPS procedure has first been described by Schnitzbauer et al. (27) and has been developed to allow for rapid liver regeneration in borderline operable patients that to not bear sufficient remnant liver to allow a complete upfront resection. The procedural steps are illustrated in FIG. 5A. Briefly, during step 1 of the ALPPS procedure the portal vein branches, feeding the tumor bearing liver, are selectively ligated, while the arterial as well as bile structures are preserved and the liver parenchyma is further transsected during this initial step of surgery. This procedure then leads to a massively augmented liver regeneration within a few days. After this substantial gain of liver regeneration, a second surgical procedure has to be performed to remove the ligated remaining liver lobes (as illustrated in FIG. 5A, step 2). The major drawback of this procedure are the high morbidity and mortality rates, and it has been under major debate to determine when regeneration has been sufficient enough to perform the second step of the resection. Accordingly, dynamical changes of miRNA ratios were analysed in 8 patients undergoing the ALPPS procedure and it was observed that, while they behaved similar as in regular liver resections during and after the step 1 (see above), during the second step of surgery (the removal of the ligated/atrophic lobe) miRNA pairs remained largely unchanged directly after surgery (step 2, difference between Pre and POD1 not significant, FIG. 5C).

Figure 5D:
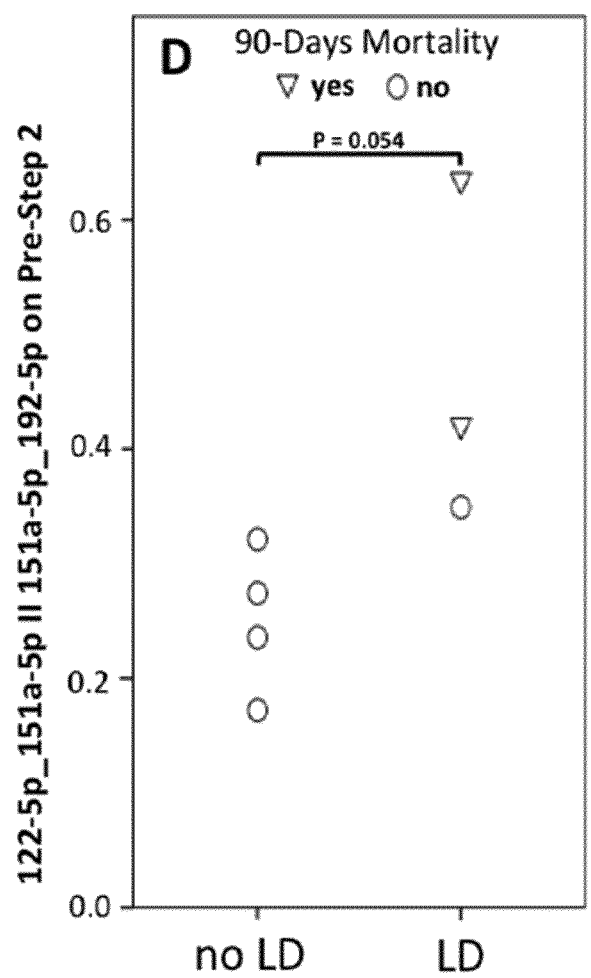

Ultimately, (D) of FIG. 5 illustrates the predictive potential of the combined miRNA pairs prior to the second step of ALLPS as stratified according to postoperative LD and mortality after the removal of the atrophic lobe. Of note, all patients that developed postoperative LD after step 2 of the ALPPS procedure showed clear changes in the miRNA signature and the resulting combined liver dysfunction probability as compared to the remaining patients (P=0.054, FIG. 5D). More importantly, the two patients that died after step 2 of the procedure both showed the highest miRNA ratio prior to the 2nd operation (FIG. 5D).

In summary, only small differences were observed in the perioperative time course of miRNA pairs between the groups (noLD, LD, ALPPS). Therefore, as an acute reaction to the operative trauma (on postoperative day 1), miRNA pairs seem to worsen fairly uniformly in all patients, regardless of their further clinical development. However, as liver function recovers after surgery, miRNA pairs seem to closely follow and normalize till postoperative day 5, with the exception of those patients at high risk of liver dysfunction. In this context, the data of the ALPPS model are of specific interest. As during the first operation, where the most significant destruction of liver tissue takes place, miRNA pairs significantly worsened. However, there was almost no difference during the step 2 of the procedure, when the atrophic liver lobe is removed (FIG. 5A). This suggests that the initial striking reduction of liver function during step 1 of ALPPS is reflected by miRNA pairs, while during step 2, when the atrophic with lobe with only limited function is removed, only minor changes occur.

Of note, the ALPPS model was also used herein to generate the presumably most interesting and clinically relevant data of this study. In particular, it was assessed if postoperative levels of miRNA pairs are able to define the optimal time point for liver surgery. It was observed that patients that did not recover well after the first step of ALPPS in terms of miRNA pairs, meaning that miRNA pairs did not return to the baseline levels, were indeed those that did very poorly after the second step of ALPPS. Indeed, the 3 patients that suffered from liver dysfunction after the 2nd step had the highest miRNA pair values and more importantly, the 2 patients that subsequently died due to "too small for size syndrome" had the 2 highest values of our ALPPS cohort.

These data show that the signature of circulating miRNAs described herein can aid in determining the optimal time point for liver resection. This is not limited to ALPPS. The miRNA signatures described herein can also be of use after portal vein embolization/ligation or to determine the optimal time point of surgery after extensive preoperative chemotherapy in high-risk patients.

TABLE 3

Characteristics of Matched Patients in Exploratory Study

| Parameter | ALPPS (N = 8) Median (range) N (%) | Major Liver Resection (N = 7) Median (range) N (%) |
|---|---|---|
| Gender | | |
| Male | 5 (62.5%) | 5 (71.5%) |
| Female | 3 (37.5%) | 2 (28.5%) |
| Age(years) | 61 (49-79) | 60 (56-82) |

TABLE 3-continued

Characteristics of Matched Patients in Exploratory Study

| Parameter | ALPPS (N = 8) Median (range) N (%) | Major Liver Resection (N = 7) Median (range) N (%) |
|---|---|---|
| Tumor Type | | |
| CRCLM | 7 | 7 |
| HCC | 1 | 0 |
| Cofactors | | |
| Neoadjuvant CTx | 6 (75%) | 7 (100%) |
| Steatosis (%) | 0 (0) | 7.5 (0-60) |
| Steatohepatitis | 0 (0%) | 1 (14%) |
| Intraoperative RBC | 1 (12.5%) | 2 (28.6%) |
| Preoperative Parameters | | |
| PDR(%) | 16 (15-17) | 21 (14-26) |
| R15(%) | 9.5 (8-10) | 6.4 (1.9-11.5) |
| SB(mg/dl) | 0.6 (0.3-2) | 0.5 (0.4-2.4) |
| AP(U/l) | 112 (80-298) | 102 (51-165) |
| GGT(U/l) | 104.5 (55-399) | 46 (16-75) |
| AST(U/l) | 31.5 (25-55) | 29 (18-49) |
| ALT(U/l) | 36 (20-56) | 20 (16-50) |
| Albumin(g/l) | 29.5 (27.9-44.1) | 28.4 (14.5-37.9) |

CRCLM = colorectal cancer liver metastases, HCC = hepatocellular carcinoma, CTx = chemotherapy, RBC = red blood cells, PDR = plasma disappearance rate, R15 = retention rate at 15 minutes, SB = serum bilirubin, PT = prothrombin time, AP = alkaline phosphatase, GGT = gamma-glutamyl transpeptidase, AST = aspartate aminotransferase, ALT = alanine aminotransferase.

REFERENCES

1. Forbes S J, Newsome P N. Liver regeneration—mechanisms and models to clinical application. Nat Rev Gastroenterol Hepatol 2016; 13:473-485.
2. Lafaro K, Buettner S, Maqsood H, Wagner D, Bagante F, Spolverato G, Xu L, et al. Defining Post Hepatectomy Liver Insufficiency: Where do We stand? J Gastrointest Surg 2015; 19:2079-2092.
3. Qadan M, Garden O J, Corvera C U, Visser B C. Management of Postoperative Hepatic Failure. J Am Coll Surg 2016; 222:195-208.
4. Hackl M, Heilmeier U, Weilner S, Grillari J. Circulating microRNAs as novel biomarkers for bone diseases—Complex signatures for multifactorial diseases? Mol Cell Endocrinol 2016; 432:83-95.
5. Bartel D P. MicroRNAs: genomics, biogenesis, mechanism, and function. Cell 2004; 116:281-297.
6. Friedman R C, Farh K K, Burge C B, Bartel D P. Most mammalian mRNAs are conserved targets of microRNAs. Genome Res 2009; 19:92-105.
7. Lecellier C H, Dunoyer P, Arar K, Lehmann-Che J, Eyquem S, Himber C, Saib A, et al. A cellular microRNA mediates antiviral defense in human cells. Science 2005; 308:557-560.
8. Mitchell P S, Parkin R K, Kroh E M, Fritz B R, Wyman S K, Pogosova-Agadjanyan E L, Peterson A, et al. Circulating microRNAs as stable blood-based markers for cancer detection. Proc Natl Acad Sci USA 2008; 105:10513-10518.
9. van Rooij E, Sutherland L B, Liu N, Williams A H, McAnally J, Gerard R D, Richardson J A, et al. A signature pattern of stress-responsive microRNAs that can evoke cardiac hypertrophy and heart failure. Proc Natl Acad Sci USA 2006; 103:18255-18260.
10. Montani F, Marzi M J, Dezi F, Dama E, Carletti R M, Bonizzi G, Bertolotti R, et al. miR-Test: a blood test for lung cancer early detection. J Natl Cancer Inst 2015, 107:djv063.
11. Sozzi G, Boeri M, Rossi M, Verri C, Suatoni P, Bravi F, Roz L, et al. Clinical utility of a plasma-based miRNA signature classifier within computed tomography lung cancer screening: a correlative MILD trial study. J Clin Oncol 2014; 32:768-773.
12. Wang J, Chen J, Sen S. MicroRNA as Biomarkers and Diagnostics. J Cell Physiol 2016; 231:25-30.
13. Strasberg S M, Phillips C. Use and dissemination of the brisbane 2000 nomenclature of liver anatomy and resections. Ann Surg. 2013; 257:377-382. doi: 310.1097/SLA.1090b1013e31825a31801f31826.
14. Rahbari N N, Garden O J, Padbury R, Brooke-Smith M, Crawford M, Adam R, Koch M, et al. Posthepatectomy liver failure: a definition and grading by the International Study Group of Liver Surgery (ISGLS). Surgery. 2011; 149:713-724. doi: 710.1016/j.surg.2010.1010.1001. Epub 211 January 1014.
15. Dindo D, Demartines N, Clavien P A. Classification of surgical complications: a new proposal with evaluation in a cohort of 6336 patients and results of a survey. Ann Surg. 2004; 240:205-213.
16. Schiergens T S, Dorsch M, Mittermeier L, Brand K, Kuchenhoff H, Lee S M, Feng H, et al. Thirty-day mortality leads to underestimation of postoperative death after liver resection: A novel method to define the acute postoperative period. Surgery 2015; 158:1530-1537.
17. Krieger P M, Tamandl D, Herberger B, Faybik P, Fleischmann E, Maresch J, Gruenberger T. Evaluation of chemotherapy-associated liver injury in patients with colorectal cancer liver metastases using indocyanine green clearance testing. Ann Surg Oncol 2011; 18:1644-1650.
18. Starlinger P, Alidzanovic L, Schauer D, Brugger P, Sommerfeldt S, Kuehrer I, Schoppmann S F, et al. Platelet-stored angiogenesis factors: clinical monitoring is prone to artifacts. Dis Markers 2011; 31:55-65.
19. Mussbacher M, Schrottmaier W C, Salzmann M, Brostjan C, Schmid J A, Starlinger P, Assinger A. Optimized plasma preparation is essential to monitor platelet-stored molecules in humans. PLoS One 2017; 12:e0188921.

20. Kocijan R, Muschitz C, Geiger E, Skalicky S, Baierl A, Dormann R, Plachel F, et al. Circulating microRNA Signatures in Patients With Idiopathic and Postmenopausal Osteoporosis and Fragility Fractures. J Clin Endocrinol Metab 2016; 101:4125-4134.
21. Blondal T, Jensby Nielsen S, Baker A, Andreasen D, Mouritzen P, Wrang Teilum M, Dahlsveen I K. Assessing sample and miRNA profile quality in serum and plasma or other biofluids. Methods 2013; 59:S1-6.
22. La Mura V, Nicolini A, Tosetti G, Primignani M. Cirrhosis and portal hypertension: The importance of risk stratification, the role of hepatic venous pressure gradient measurement. World J Hepatol 2015; 7:688-695.
23. Stremitzer S, Tamandl D, Kaczirek K, Maresch J, Abbasov B, Payer B A, Ferlitsch A, et al. Value of hepatic venous pressure gradient measurement before liver resection for hepatocellular carcinoma. Br J Surg 2011; 98:1752-1758.
24. Boleslawski E, Petrovai G, Truant S, Dharancy S, Duhamel A, Salleron J, Deltenre P, et al. Hepatic venous pressure gradient in the assessment of portal hypertension before liver resection in patients with cirrhosis. Br J Surg. 2012; 99:855-863. doi: 810.1002/bjs.8753. Epub 212 April 1017.
25. Hidaka M, Takatsuki M, Soyama A, Tanaka T, Muraoka I, Hara T, Kuroki T, et al. Intraoperative portal venous pressure and long-term outcome after curative resection for hepatocellular carcinoma. Br J Surg. 2012; 99:1284-1289. doi: 1210.1002/bjs.8861.
26. Haegele S, Reiter S, Wanek D, Offensperger F, Pereyra D, Stremitzer S, Fleischmann E, et al. Perioperative Non-Invasive Indocyanine Green-Clearance Testing to Predict Postoperative Outcome after Liver Resection. PLoS One 2016; 11:e0165481.
27. Schnitzbauer A A, Lang S A, Goessmann H, Nadalin S, Baumgart J, Farkas S A, Fichtner-Feigl S, Lorf T, Goralcyk A, Horbelt R, Kroemer A, Loss M, Rummele P, Scherer M N, Padberg W, Konigsrainer A, Lang H, Obed A, Schlitt H J. Right portal vein ligation combined with in situ splitting induces rapid left lateral liver lobe hypertrophy enabling 2-staged extended right hepatic resection in small-for-size settings. Ann Surg 2012; 255:405-414.

The invention claimed is:

1. A method of treating a subject suffering from malignant lesions in the liver, benign hepatic neoplasms, hepatic cysts, intrahepatic gallstones and/or parasites, said method comprising the steps of:
   a) providing a blood sample from said subject before partial liver resection,
   b) determining in said sample the expression level of miR-151a and miR-192, and optionally of miR-122, and
      i. identifying the ratios of miR-151a to miR-192, and optionally of miR-122 to miR-151a, based on the expression levels determined in b), comparing said expression level ratios with reference expression level ratios, and determining standard deviations between the compared expression level ratios, or
      ii. comparing the expression levels of miR-151a, miR-192 and miR-122 with reference expression levels and determining standard deviations between the compared expression levels, and
   c) classifying the sample from the outcome of step i) or step ii) into one of at least two classes, namely a "high-risk" of liver dysfunction after partial liver resection and a "low-risk" of liver dysfunction after partial liver resection, wherein a difference of expression levels or expression level ratios of less than 1 standard deviation classifies the sample as "low-risk" and a difference of expression levels or expression level ratios of more than 1.5 standard deviations classifies the sample as "high-risk", and
   d) performing partial liver resection on the subject from which the sample was obtained when the sample is classified as "low-risk", and performing liver transplantation, chemotherapy, immunotherapy, radiofrequency ablation, portal vein embolization, and/or transarterial chemoembolization (TACE) on the subject from which the sample was obtained when the sample is classified as "high-risk".

2. The method of claim 1, wherein in step (b)(i) the expression levels of miR-151a, miR-192 and miR-122 are determined.

3. The method of claim 1, wherein the subject is subjected to liver regeneration stimulation prior to the partial liver resection.

4. The method of claim 1, wherein the reference expression level is the expression level of at least one miRNA selected from the group consisting of miR-151a, miR-192 and miR-122 of a healthy subject or of a subject without post-operative liver dysfunction or of a group thereof.

5. The method of claim 1, wherein reference expression level ratios are expression level ratios of miR-151a to miR-192 and of miR-122 to miR-151a of a healthy subject or of a subject without post-operative liver dysfunction or of a group thereof.

6. The method of claim 3, wherein the liver regeneration stimulation is selected from the group consisting of induction of portal vein embolization, associating liver partition and portal vein ligation for staged hepatectomy (ALPPS), exercise intervention ("prehabilitation") dietary intervention, and pharmacological therapy reducing portal vein hypertension.

7. The method of claim 1, wherein the blood sample is selected from the group consisting of serum, plasma, and platelet-poor plasma.

8. The method claim 1, wherein the expression levels or expression level ratios of the sample are compared with the reference expression level or expression level ratios using a classification model.

9. The method of claim 8, wherein the classification model is selected from the group consisting of logistic regression models, support vector machine models and decision tree models.

10. The method of claim 1, wherein the expression levels are determined using a method selected from the group consisting of a sequencing-based method, an array-based method and a PCR-based method.

11. The method of claim 1, wherein the malignant lesions in the liver are caused by a condition selected from the group consisting of metastatic colorectal cancer, hepatocellular carcinoma, and cholangiocellular carcinoma.

12. The method of claim 10, wherein the PCR-based method is a quantitative PCR-based method or the sequencing-based method is a high-throughput sequencing technology.

13. The method of claim 1, wherein the liver malignancy is primary liver cancer or secondary liver cancer.

* * * * *

SEQUENCE LISTING

<160> NUMBER OF SEQ ID NOS: 6

<210> SEQ ID NO 1
<211> LENGTH: 22
<212> TYPE: RNA
<213> ORGANISM: Artificial Sequence
<220> FEATURE:
<223> OTHER INFORMATION: hsa-miR-122-5p

<400> SEQUENCE: 1
uggaguguga caaugguguu ug                                              22

<210> SEQ ID NO 2
<211> LENGTH: 21
<212> TYPE: RNA
<213> ORGANISM: Artificial Sequence
<220> FEATURE:
<223> OTHER INFORMATION: hsa-miR-192-5p

<400> SEQUENCE: 2
cugaccuaug aauugacagc c                                               21

<210> SEQ ID NO 3
<211> LENGTH: 21
<212> TYPE: RNA
<213> ORGANISM: Artificial Sequence
<220> FEATURE:
<223> OTHER INFORMATION: hsa-miR-151a-5p

<400> SEQUENCE: 3
ucgaggagcu cacagucuag u                                               21

<210> SEQ ID NO 4
<211> LENGTH: 85
<212> TYPE: RNA
<213> ORGANISM: Artificial Sequence
<220> FEATURE:
<223> OTHER INFORMATION: hsa-miR-122

<400> SEQUENCE: 4
ccuuagcaga gcuguggagu gugacaaugg uguuuguguc uaaacuauca aacgccauua     60
ucacacuaaa uagcuacugc uaggc                                           85

```
<210> SEQ ID NO 5
<211> LENGTH: 110
<212> TYPE: RNA
<213> ORGANISM: Artificial Sequence
<220> FEATURE:
<223> OTHER INFORMATION: hsa-miR-192

<400> SEQUENCE: 5
gccgagaccg agugcacagg gcucugaccu augaauugac agccagugcu cucgucuccc         60
cucuggcugc caauuccaua ggucacaggu auguucgccu caaugccagc                   110

<210> SEQ ID NO 6
<211> LENGTH: 90
<212> TYPE: RNA
<213> ORGANISM: Artificial Sequence
<220> FEATURE:
<223> OTHER INFORMATION: hsa-miR-151a

<400> SEQUENCE: 6
uuuccugccc ucgaggagcu cacagucuag uaugucucau ccccuacuag acugaagcuc         60
cuugaggaca gggaugguca uacucaccuc                                          90
```